United States Patent
Paull et al.

(10) Patent No.: US 6,495,743 B1
(45) Date of Patent: Dec. 17, 2002

(54) PLANT XYLANASES

(75) Inventors: Robert E. Paull; Nancy Jung Chen, both of Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 09/595,857

(22) Filed: Jun. 16, 2000

Related U.S. Application Data

(60) Provisional application No. 60/141,543, filed on Jun. 28, 1999.

(51) Int. Cl.$^7$ .................. C07H 21/04; A01H 11/00; A01H 5/00; C12N 5/04; C12N 15/82; C12N 15/74
(52) U.S. Cl. .................... 800/298; 536/23.1; 536/23.6; 800/295; 800/287; 435/419; 435/468; 435/471
(58) Field of Search ................................. 800/290, 298, 800/287; 435/320.1, 468, 470, 419; 536/23.1, 23.6

(56) References Cited

PUBLICATIONS

Banik, M., et al., Molecular cloning of cDNAs encoding (1→4)–β–xylan endohydrolases from the aleurone layer of germinated barley (*Hordeum vulgare*), Plant Molecular Biology 31:1163–1172 (1996).

Fitch, M.M.M., et al., Genetic Transformation in *Carica papaya*L. (Papaya), Biotechnology in Agriculture and Forestry, 29:236–256 (1994).

Fitch, M.M.M., et al., "Transgenic papaya plants from Agrobacterium–mediated transformation of somatic embryos", Plant Cell Reports 12:245–249 (1993).

Fitch, M.M.M., et al., "Stable transformation of papaya via microprojectile bombardment", Plant Cell Reports 9:189–194 (1990).

Maclachlan, G., et al., Endo–1, 4–β–Glucanase, Xyloglucanase, and Xyloglucan Endo–Transglycosylase Activities Versus Potential Substrates in Ripening Tomatoes[1] Plant Physiol 105:965–974 (1994).

Paull, Robert E., et al., "Changes in papaya cell walls during fruit ripening", Postharvest Biology and Technology, 16:79–89 (1999).

Paull, Robert E., et al., Postharvest Variation in Cell Wall––Degrading Enzymes of Papaya (*Carica papaya*L. ) during Fruit Ripening[1], Plant Physiol. 72:382–385 (1983).

Paull, Robert E., et al., Postharvest handling and losses during marketing of papaya (*Carica papaya*L.), Postharvest Biol. and Tech. 11:165–179 (1997).

Rose, J. K.C., et al., "Temporal Sequence of Cell Wall Disassembly in Rapidly Ripening Melon Fruit" Plant Phys. 117:345–361 (1998).

Seymour, G.B., et al., "Cell wall disassembly and fruit softening", Postharvest News and Information 7: (3) 45N–52N (1996).

Lashbrook, C.C., et al., "Non–Pectolytic Cell Wall Metabolism During Fruit Ripening", Fruit Molecular Biology (1998) (In Press–Preprint provided by senior author.).

*Primary Examiner*—Elizabeth F. McElwain
*Assistant Examiner*—Stuart Baum
(74) *Attorney, Agent, or Firm*—Morrison & Foerster LLP

(57) ABSTRACT

The isolation, purification, cloning and expression of a papaya xylanase gene is presented. This gene can be utilized to identify other related xylanase genes from other plants, especially dicots. Once cloned, xylanase genes can be utilized to create transgenic plants exhibiting controlled growth, abscission, dehiscence and/or fruit and vegetable ripening characteristics.

11 Claims, No Drawings

US 6,495,743 B1

PLANT XYLANASES

RELATED APPLICATION

This application claims priority under 35 U.S.C. §119(e) of U.S. provisional patent application No. 60/141,543, filed Jun. 28, 1999, which is hereby incorporated by reference in its entirety.

Research related to the present invention was supported in part by the United States Department of Agriculture Grant 59-5320-4-569. The government may have certain rights to this invention.

FIELD OF THE INVENTION

This invention is in the field of molecular biology. In particular, this invention relates to the isolation, purification, cloning and expression of plant xylanases, nucleotide sequences encoding plant xylanases and further relates to the control of fruit and vegetable softening, as well as the control of growth, abscission and dehiscence in plants.

BACKGROUND OF THE INVENTION

The ability to market high quality fruits and vegetables is dependent upon on the control and regulation of several interrelated factors. These factors include the regulation and control of plant growth, abscission and dehiscence processes as well as the control of softening of fruits and vegetables.

Xylans are a significant component of plant cell walls and are regarded as hemicellulose. Xylanases are enzymes involved in the breakdown and release of xylose oligomers from cell wall xylans. Xylanases are grouped with other cell wall hydrolases that degrade hemicelluloses and are referred to as hemicellulases. However, the role of hemicellulases in wall softening has not received much study (Lashbrook et al., 1998). For convenience sake, each of the references and articles cited herein are listed with their complete citations at the end of the application before the claims section.

Abscission is a process involved in the loss of vegetative buds, branches, roots, sepals, petals, anthers, ovaries, fruit, leaves, fruit, and flowers in plants in response to developmental cues (e.g. Infertile flower, leaf senescence, ripe fruit, etc) and environmental stresses (e.g. Frost, insufficient light, high temperature, defense reaction to herbivore, fungi and bacteria) (Sexton, 1995). As such, control of abscission is critical to maximizing yields and fruit and vegetable quality. Abscission is an active metabolic process resulting in the weakening of the cell walls, of anything from 1 to 20 rows of cells in genetically determined abscission zones. Cell wall hydrolases such as polygalacturonase, glucanases, pectin methyl esterase, cellulases and hemicellulases are thought to be involved.

Dehiscence is the spontaneous and sometimes violent opening of a fruit, seed pod, or anther to release the seed or pollen. This process shares a number of feature in common with abscission. Both dehiscence and abscission are a consequence of cell wall dissolution at a predetermined position. Cell wall hydrolases such as glucanases, polygalacturonases and hemicellulases are possibly involved.

During the final stage of fruit development, ripening occurs that involves a number of changes and an important change is softening. This softening is thought to be the result of cell wall modification due to the activity of cell wall hydrolases. These hydrolases are developmentally regulated during fruit ripening. Fruit and vegetable ripening and associated cell wall changes often involves increases in exo- and endo-polygalacturonase, pectin methyl esterase, cellulase, glucanase, xyloglucanase, xyloglucan endo-transglycosylase and xylanase activities. Transgenic plants with antisense constructs to many of these enzymes to inhibit activity have not reduced fruit softening (Arrowsmith and de Silva, 1995; Brummell et al., 1994; Giovannoni et al., 1989; Tieman et al., 1992). Plants with reduced xylanase activity have not, as yet, been created.

Plant cell wall breakdown is important element in the loss of structural integrity and hence plays an important role in growth, abscission, dehiscence and fruit softening. There is an overlap between the cell wall changes that occur during fruit softening and the wall changes that occur during growth, dehiscence and abscission (Taiz, 1984; Lashbrook et al., 1994; Kalaitzis et al., 1997; Lashbrook et al., 1998; McManus et al., 1998; Peterson et al., 1996; Jenkins et al., 1996; Meakin and Roberts, 1990; Jenkins et al., 1994; Osborne, 1989; Fischer and Bennett, 1991). The processes all involve coordinated wall breakdown and in the case of dehiscence and abscission involve wall separation. While much is known about abscission, dehiscence and fruit ripening processes generally in plants, little is known about the role of plant xylanases in growth, abscission, dehiscence and fruit softening in these processes.

There is thus a need to identify plant xylanase genes and gene products and to determine their role in growth, abscission and dehiscence as well as fruit and vegetable ripening and softening. In particular, there is a need to isolate, purify and clone xylanase genes and gene products so that xylanase activity may be controlled and regulated in plants.

SUMMARY OF THE INVENTION

In order to meet these needs, the present invention is directed to purified, isolated, sequenced and cloned plant xylanase. The present invention is further directed to transgenic plants expressing cloned xylanase genes. In the transgenic plants of the invention, dehiscence and abscission processes and/or fruit and vegetable ripening processes are controlled and/or regulated.

The xylanase DNA of the invention may be isolated from any plant, preferably a dicotyledenous plant. Representative dicotyledenous plants include but are not limited to papayas, tomatoes, eggplant, potato, cabbage, broccoli, cauliflower, celery, mango, pears, plum, papayas, melons, cucumbers, avocados, peaches, apples, apricots, grapes, cherries, plums, nectarines, kiwi, raspberry, strawberries, lettuce, cranberry, sugar beet, tobacco, walnut, almond, cotton, sesame, oilseed rape, flax, soybeans, peas and the like. Representative monocotyledenous plants include, but are not limited to banana, pineapple and the like.

In general, the invention features substantially pure xylanase DNA or protein obtained from a plant, more particularly a dicotyledenous plant, most particularly a papaya. The xylanase protein of the invention is capable of hydrolyzing xylan 1,4-beta-xylose-xylose bonds.

The xylanase protein of the invention comprises polypeptide sequences substantially identical to the sequences shown in SEQ ID NO:1, SEQ ID NO:2, SEQ ID NO:3, SEQ ID NO:4 or SEQ ID NO:25.

In another related aspect, the invention features substantially pure DNA having a sequence substantially identical to the nucleotide sequence shown in SEQ ID NO: 24 or functional equivalents thereof. Such nucleotide sequences include those shown in SEQ ID NO:26–SEQ ID NO:33. In preferred embodiments, such DNA is cDNA or is genomic DNA. As will be apparent to those skilled in the art, functional equivalents of the invention include, for example, those nucleotide sequences which encode the same polypeptide (but which by virtue of the degeneracy of the genetic code posses a different nucleotide sequence); sequence which code substantially the same polypeptide but wherein there may be more conserved amino acid substitution (i.e. the substitution of an amino acid for one similar properties); sequences which encode substantially the same polypeptide (which preferably share 50% amino acid identity and more preferably 60% identity) but wherein there may be one or more amino acids deletions or truncations; and sequence which hybridize under standard conditions to the complete nucleotide shown in SEQ ID NO: 24. A functional equivalent would be an antisense nucleotide sequence. In a related aspect, the DNA of the invention may be linked to a heterologous nucleic acid. Such heterologous nucleic acide can be any nucleotide sequence different from that of the xylanase DNA of the invention. The heterologous DNA may be a promoter. In related aspects, the invention also features a vector and a cell (e.g., a plant) which includes such substantially pure xylanase DNA. In various preferred embodiments, the vector-containing cell is a prokaryotic cell, for example, E. coli or Agrobacterium or, more preferably, a plant cell.

The invention is further directed to isolated and purified oligonucleotides having nucleotide sequences substantially identical to those sequences selected from SEQ ID NO:5–SEQ ID NO:23.

The invention also provides a method for isolation from a plant a DNA sequence encoding an xylanase comprising, probing a DNA library prepared from plant tissue with oligonucleotide probes comprising a conserved sequence from plant xylanase, particularly papaya endo-β-1,4-xylanase cDNA. The library can either be genomic or cDNA. The most preferred nucleotide sequences for papaya are xyl-31, xyl-32, xyl-41, xyl-42, xyl-43 and xyl-44, SEQ ID NO:18–SEQ ID NO:23. The preferred sequences for general isolation from other plant species for those skilled in the art would be xyl-11 to xyl-23, SEQ ID NO:5 to SEQ ID NO:17.

The present invention further includes multiple types of xylanase nucleic acid constructs including (1) "sense" constructs encoding xylanase proteins, which can increase or reduce the expression of xylanase in plant species and (2) "antisense" constructs containing DNA, which can be used to produce xylanase antisense RNA to reduce expression of xylanase in plants. Optimal amounts of antisense RNA in transgenic plants will selectively inhibit the expression of genes in these plants which are involved in xylanase activity. The constructs may include nucleotides capable of encoding peptides having sequences such as SEQ ID NO:4 and 25.

Some of these constructs will direct constitutive production of transcripts. Other constructs will direct expression in specific organs and/or specific tissue layers of the transgenic plant. These organs will include leaves, petioles, stems, flower organs, seeds, fruits or photosynthetically active parts of the plant. Tissue layers will include but may not be restricted to the epidermis and adjacent cell layers. Such organ and tissue specific expression can be directed by organ and tissue specific promoters.

The present invention also provides recombinant cells and plants containing these constructs. The constructs are introduced into recombinant plants by transformation.

In one embodiment, the first category of DNA constructs include: a promoter selected from but not limited to constitutive, tissue-specific, fruit-specific, cell-type specific, seed-specific, flower-specific, fruit-specific, epidermis-specific promoters, a promoter specific to cell layers adjacent to the epidermis or a promoter specific to photosynthetically active plant tissues, which functions in plant cells to cause the production of an RNA sequence. In this embodiment, the DNA coding region sequences encode proteins which can be used to increase the activity of plant xylanase in transgenic plants. The DNA coding region will further include a region 3' to the coding regions the 3' nonranslated region which functions in plant cells to cause the addition of polyadenylate nucleotides to the 3' end of the RNA sequence promoter.

In another embodiment, a second category of DNA construct will include a constitutive promoter, seed-specific, flower-specific, fruit-specific, abscission zone-specific, dehiscence-zone specific, epidermis-specific promoter, a promoter specific to cell layers adjacent to the epidermis or a promoter specific to photosynthetically active plant tissues, which functions in plant cells to cause the production of an RNA sequence. The DNA construct will also include DNA sequences which can produce antisense RNA molecules. These RNA molecules can selectively inhibit the accumulation of transcripts encoding proteins which encode plant xylanase thereby reducing xylanase expression and activity.

In accordance with another aspect of the present invention, there is provided a method of producing genetically transformed plants which express a gene or genes involved in xylanase activity. In this method, a recombinant, double-stranded DNA molecule is introduced into the genome of a plant cell. In this embodiment, the DNA sequence will include a promoter which functions in plant cells to cause the production of an RNA sequence in flowers, seeds, fruit, other plant tissues or organs achieved, for example, by use of tissue specific promoters to regulate transcription of the introduced sequence. In addition, the sequence will include a DNA coding sequence encoding proteins involved in xylanase activity in plants. Alternatively, the sequence will be a template to the synthesis of antisense RNA inhibiting xylanase activity. The DNA sequence will also include a 3' non-translated region which functions in plant cells to cause the addition of polyadenylate nucleotides to the 3' end of the RNA sequences. The method also includes obtaining transformed plant cells and regenerating from the transformed plant cells genetically transformed plants. The DNA sequence can be introduced into a plant by a sexual cross.

The present invention is also directed to transgenic cells such as bacterial, yeast, fungi, plant and mammalian cells expressing the DNA sequences of this invention. The present invention is also directed to purified xylanase protein isolated from the transgenic cells of the invention. The present invention is also directed to purified antibodies directed to the xylanase protein of the invention. The antibodies may be monoclonal or polyclonal.

BRIEF DESCRIPTION OF THE SEQUENCE LISTING

SEQ ID NO: 1–SEQ ID NO: 4 show peptides sequences obtained by sequencing purified papaya xylanase protein.

SEQ ID NO: 5–SEQ ID NO: 17 show the sequences of degenerate primers based upon the amino acid sequence of purified papaya xylanase.

SEQ ID NO: 18–SEQ ID NO: 23 show the sequences of papaya xylanase gene specific oligonucleotide primers.

SEQ ID NO: 24 shows a full length cDNA sequence for a papaya xylanase cDNA clone.

SEQ ID NO: 25 shows the peptide sequence of the papaya xylanase derived from the cDNA sequence.

SEQ ID NO:26–SEQ ID NO:33 show nucleotide sequences substantially identical to papaya xylanase.

DETAILED DESCRIPTION OF THE INVENTION

DEFINITIONS

To ensure a complete understanding of the invention, the following definitions are provided:

Xylan: The plant hemicellulose component, endo-1,4-beta-Xylan (xylan) is a heteropolymer of the pentose sugar D-xylose linked by 1,4-beta-xylosidic bonds. Xylan is a component of the plant cell wall hemicellulose fraction. Arabinose, glucuronic acid, galactose and other sugars occur as monomers or short oligomers attached as side chains at either or both the 2- or 3-O position on the xylose residues of the xylan backbone. These side chains are sometimes modified with acetyl ester or methyl ester groups, Xylanase: Endo-1,4 beta-xylanase (xylanase) is an enzyme that catalyse the hydrolysis of the 1,4-beta-xylose-xylose bonds mid-chain in xylans. The endo-hydrolysis of the 1,4 beta-xylansidic linkage generates xylo-oligomers. Each plant species may contain a family of xylanase heteroallelic genes. The genes in the xylanase family may be identifiable by, for example, their nucleotide sequence, the temporal pattern of their expression and the tissue in which they are expressed.

Encoding: Encoding an endo-1,4-beta-xylanase is a nucleotide sequence or DNA sequence of the invention is a sub-sequence or a full length polynucleotide sequence which when present in the cell, expresses and endo-xylanase polypeptide. In the case where the inserted polynucleotide sequence is transcribed and translated to produce a polypeptide, one of skill will recognize that because of codon degeneracy a number of polynucleotides will encode the same polypeptide. These variants are specifically covered by the above term. Further included in the above term are proteins and peptides that retain immulogical reactivity to antibodies raised against the naturally occurring protein.

Plant: Plant includes whole plants, plant organs (e.g. leaves, stems, roots, etc.) seeds and plant cells.

Transgenic Plants: Transgenic plants are plants which contain DNA sequences which were introduced by transformation.

Dicotyledons and monocotyledons: Flowering plants are grouped into two classes: dicotyledons (dicots) and monocotyledons (monocots). In addition to other differences, dicotyledons have an embryo with two cotyledons as compared to monocotyledons which have a single cotyledon. Representative dicots useful in the invention include papaya, tomato, melons, cucumbers, Capsicum species, strawberries, peaches, apples, apricots, cherries, plums, nectarines, cucumbers, avocados, grapes, peanuts, sunflower, cotton, sesame, oilseed rape, field mustard, turnip, Brassica species, coffee, almonds, walnut, pistachio, beans, Rubus species, citrus, passion fruit, mango, rambutan, carambola, durian, litchi, annona species, soybeans, and peas. Representative monocots useful in the invention include banana, asparagus, pineapple, onion, orchids, dates, grain crops including cereals, coconut and other palms.

Promoter: A promoter is the minimal DNA sequence sufficient to direct transcription. Promoters can render transcription controllable for cell-type specific, tissue-specific, organ specific, or inducible expression. Promoter elements may be located in the 5' or 3' regions of the native gene.

Poly-A Addition Site: A poly-A addition site is a nucleotide sequence which causes certain enzymes to cleave mRNA at a specific site and to add a sequence of adenylic acid residues to the 3'-end of the mRNA.

Polypeptide: Polypeptide means any chain of amino acids, regardless of length or post-translational modification (e.g., glycosylation or phosphorylation).

Substantially Identical: For a polypeptide, substantially identical means a polypeptide exhibiting at least 50%, preferably 70%, more preferably 90%, and most preferably 95% identity to a reference polypeptide. For a nucleic acid substantially identical means a nucleic acid sequence exhibiting at least 85%, preferably 90%, more preferably 95%, and most preferably 97% identity to a reference nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 30 nucleotides, preferably at least 60 nucleotides, more preferably at least 75 nucleotides, and most preferably 110 nucleotides. Sequence identity is typically measured using sequence analysis software (e.g., Sequence Analysis Software Package of the Genetics Computer Group (GCG), University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; phenylalanine, and tyrosine.

Substantially Pure Polypeptide: Substantially pure polypeptide means a xylanase polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight xylanase polypeptide. A substantially pure xylanase polypeptide may be obtained, for example, by extraction from a natural source (e.g., a plant) by expression of a recombinant nucleic acid encoding a xylanase polypeptide; or by chemically synthesizing the protein. Purity can be measured by any appropriate method, e.g., column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include, without limitation, those derived from eukaryotic organisms but synthesized in E. coli or other prokaryotes, or those derived from a eukaryotic cell which does not normally synthesize such a protein, or those derived from a eukaryotic cell engineered to overexpress such a protein.

Substantially Pure DNA: Substantially pure DNA means DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

Transformed Cell: Transformed cell means a cell into which (or into an ancestor of which) has been introduced, by means of recombinant DNA techniques, a DNA molecule encoding (as used herein) a xylanase polypeptide.

Positioned for Expression: Positioned for expression means that the DNA molecule is positioned adjacent to a DNA sequence which directs transcription and translation of the sequence (i.e., facilitates the production of, e.g., a recombinant xylanase polypeptide or RNA molecule).

Operably Linked: Operably linked mean that a gene and a regulatory sequence(s) are connected in such a way as to permit gene expression when the appropriate molecules (e.g., transcriptional activator proteins) are bound to the regulatory sequence(s).

Antisense: Antisense technology is utilized to shut off endogenous genes. Cells are infected with a vector that carries a portion of a target gene such as axylanase gene. The orientation of the gene in the vector is backward so that the RNA transcribed is complementary in sequence to the mRNA transcribed from the corresponding cellular gene. If the complementary (antisense) RNA is present in large excess, it base pairs to virtually all of the mRNA to form a double stranded RNA that cannot be translated into protein and is generally rapidly destroyed. The effect of the use of the antisense technology is that the protein product (e.g. xylanase) of the target gene is not produced.

Purified Antibody: Purified antibody means an antibody which is at least 60%, by weight, free from proteins and naturally-occurring organic molecules with which it is naturally associated. Preferably, the preparation is at least 75%, more preferably 90%, and most preferably at least 99%, by weight, antibody, e.g., a plant xylanase specific antibody. A purified xylanase antibody may be obtained, for example, by affinity chromatography using recombinantly-produced xylanase protein or conserved motif peptides and standard techniques.

Specifically Binds: Specifically binds means an antibody which recognizes and binds xylanase protein but which does not substantially recognize and bind other molecules in a biological sample.

DETAILED DESCRIPTION OF THE INVENTION

Taking into account these definitions, the present invention is directed to isolated, purified and cloned plant xylanase. In addition, this invention is directed to transgenic plants expressing cloned xylanases.

Xylans are a significant component of dicot and monocot cell walls (Carpita and Gibeaut, 1993) while xylanase proteins have been studied in a only a few plants. Both xylosidase and endo-xylanase have been reported in avocado fruit (Ronen et al., 1991), papaya fruit (Paull and Chen, 1983; Egusa and Paull, 1991), pear fruit (Labavitch and Greve, 1983) and Japanese pear fruit (Yamaki and Kakiuchi, 1979), while endo-xylanase increases during cucumber fruit ripening (Miller et al., 1989). In Japanese pear fruit, the soluble xylanase protein increases, then decreases while bound xylanase continues to increase during ripening (Yamaki and Kakiuchi, 1979). In avocado fruit, endo-xylanase is present at harvest and increases slightly during softening, while xylosidase activity doubles in activity (Ronen et al., 1991). In Japanese pear fruit and papaya fruit, both xylosidase and endo-xylanase increase markedly during ripening (Yamaki and Kakiuchi, 1979; Paull and Chen, 1983). Xylanase activity is induced in cucumber fruit tissue subject to mechanical stress (Miller et al., 1987), though no softening was noted. Xylanase has been reported from Acacia cultured cells (Lienart et al., 1985) and from barley aleurone layers during germination, but not in young barley leaves (Banik et al., 1996). Cell wall hydrolases may have a role in cell growth (Taiz, 1984), however, no role has yet been ascribed to xylanase. There have been no reports of plant endoxylanase during abscission or dehiscence. The failure to detect xylanase during abscission or dehiscence or in other fruit during ripening or softening may reflect species specificity, very low levels of activity, the presence of inhibitors, association of the xylanase with wall polymers regulating its activity or the absence.

While much is known about xylanase activity from plant pathogens (Doux-Gayat et al., 1978) and from microorganisms (Wong et al., 1988), little is known about the genes encoding plant xylanases, particularly xylanase genes isolated from dicots. A cDNA clone of endo-xylanase has been isolated from barley aleurone during germination (Banik et al., 1996) and endo-xylanase like sequences have been found Arabidopsis. Cell wall hydrolases, other than polygalacturonase, glucanase, cellulase, xyloglucanase, xyloglucan endo-tranglycosylase, and galactosidase, have been suggested as having a role in fruit softening during fruit ripening (Lashbrook et al., 1998). These suggestions are based frequently on cell wall breakdown studies such as from melon fruit (Rose et al., 1998) and papaya fruit (Paull et al., 1998).

There is thus a need to isolate and clone genes encoding xylanases in various dicots. It is appreciated by those skilled in the art of molecular biological techniques that the cloning of a dicot xylanase gene provides for the ability to identify, characterize and analyze other dicot xylanase genes.

The nucleotide sequences of the subject invention are used to identify other dicot xylanase genes and to detect differences in the sequences of xylanase genes between various dicots. The nucleotide sequences of the subject invention are also utilized to determine expression of the xylanase gene in various cell types.

Nucleotide sequences encoding a portion of a dicot xylanase gene and the gene product produced therefrom have numerous applications in techniques known to those skilled in the art of molecular biology. These techniques include use as PCR probes, use as hybridization probes, use in chromosome and gene mapping, use in the recombinant production of proteins encoded by the nucleotide sequence, generation of anti-sense RNA, DNA or nucleotide analogues and the like. The uses of the nucleotide sequences provided for in this application are exemplary of known techniques and are not intended to reflect any limitation on their use in any technique that would be known to the person of ordinary skill in the art. Furthermore, the nucleotide sequences provided for in this application may be used in molecular biology techniques that have not yet been developed, provided the new techniques rely on properties of polynucleotide sequences that are currently known to the person of average skill in the art, e.g., the triplet genetic code, specific base pair interactions, etc.

One aspect of this invention is the identification of the chromosomal location of the xylanase gene in dicots thereby enabling one of ordinary skill in the art to orient genetic maps from various dicots. The nucleotide sequences provided herein may be mapped to chromosomes and specific regions of chromosomes using well-known genetic and/or chromosomal mapping techniques. These techniques include in situ hybridization, linkage analysis against known chromosomal markers, hybridization screening with libraries or flow-sorted chromosomal preparations specific to known chromosomes, and the like. Fluorescent in situ hybridization of chromosomal preparations and other physical chromosome mapping techniques, may be correlated with additional genetic map data. Examples of genetic map data can be found, for example, in *Genetic Maps: Locus Maps of Complex Genomes, Book 5: Human Maps*, O'Brien, editor, Cold Spring Harbor Laboratory Press (1990).

Nucleotide sequences encoding xylanase genes may be joined to a variety of other nucleotide sequences of interest by means of well established recombinant DNA techniques (see, for example, Ausubel, et al.,(1987).

Nucleotide sequences which are appropriate for joining to xylanase sequences include an assortment of cloning vectors, e.g., plasmids, cosmids, lambda phage derivatives, phagemids, and the like, that are in the public domain. Vectors of interest include expression vectors, replication vectors, probe generation vectors, sequencing vectors, and the like. In general, vectors of interest may contain an origin of replication functional in at least one organism, convenient restriction endonuclease digestion sites, and selectable markers for the host cell.

Another aspect of the subject invention is to provide for xylanase-specific nucleic acid hybridization probes capable of hybridizing with naturally occurring nucleotide sequences encoding xylanases. Nucleic acid hybridization probes for the detection of xylanase encoding nucleotide sequences should preferably contain at least 50% of the nucleotides from the sequence of a given xylanase encoding nucleotide sequence. The hybridization probes of the subject invention may be derived from the nucleotide sequences of the cDNA and the genomic sequences encoding xylanases uniquely identified by the nucleotide sequences of the xylanase gene. Hybridization probes may be labeled by a variety of reporter groups, including fluorescent labels, chemilumenscence radionuclides such as $^{32}$P or $^{35}$S, or enzymatic labels such as alkaline phosphatase, coupled to the probe via avidin/biotin coupling systems, and the like.

New xylanase genes and gene products may be identified by database analysis. The dicot xylanase sequence maybe compared to sequences in various databases such as Swiss Prot, Genbank and the like. Sequences with approximately 50% similarity to the xylanase gene of the invention may be selected and analyzed for further study.

In addition to database analysis, the isolation of additional plant xylanases is made possible using standard molecular biology techniques. In particular, using all or a portion of the amino acid sequence of a plant xylanase of the invention, one may readily design xylanase oligonucleotide probes, including xylanase degenerate oligonucleotide probes (i.e., a mixture of all possible coding sequences for a given amino acid sequence). These oligonucleotides may be based upon the sequence of either strand of the DNA comprising the motif. General methods for designing and preparing such probes are provided, for example, in *Guide to Molecular Cloning Techniques*, 1987, S. L. Berger and A. R. Kimmel, eds., Academic Press, New York and in *Molecular Cloning.*

*A laboratory Manual.* 1989. $2^{nd}$ Edition. J. Sambrook, E. F. Fritsch, T Maniatis Cold Spring Harbor, New York. These oligonucleotides are useful for xylanase gene isolation, either through their use as probes capable of hybridizing to xylanase complementary sequences or as primers for various polymerase chain reaction (PCR) cloning strategies. In one particular example, isolation of other xylanase genes is performed by PCR amplification techniques well known to those skilled in the art of molecular biology using oligonucleotide primers designed to amplify only sequences flanked by the oligonucleotides in genes having sequence identity to xylanase of the invention. The primers are optionally designed to allow cloning of the amplified product into a suitable vector.

Hybridization techniques and procedures are well known to those skilled in the art. If desired, a combination of different oligonucleotide probes may be used for the screening of the recombinant DNA library. The oligonucleotides are labeled with $^{32}$P using methods known in the art, and the detectably-labelled oligonucleotides are used to probe filter replicas from a recombinant DNA library. Recombinant DNA libraries may be prepared according to methods well known in the art or may be obtained from commercial sources as described above.

For detection or isolation of closely related xylanases, high stringency conditions may be used; such conditions include hybridization at about 42° C. and about 50% formamide; a first wash at about 65° C., about 2×SSC, and 1% SDS; followed by a second wash at about 65° C. and about 0.1% SDS, 1×SSC. Lower stringency conditions for detecting xylanase genes having about 85% sequence identity to the xylanase gene described herein include, for example, hybridization at about 42° C. in the absence of formamide; a first wash at about 42° C., about 6×SSC, and about 1% SDS; and a second wash at about 50° C., about 6×SSC, and about 1% SDS.

Xylanase oligonucleotides may also be used as primers in PCR cloning strategies. Such PCR methods are well known in the art and described, for example, in PCR Technology, H. A. Erlich, ed., Stockton Press, London, 1989; PCR Protocols: A Guide to Methods and Applications, M. A. Innis, D. H. Gelfand, J. J. Sninsky, and T. J. White, eds., Academic Press, Inc., New York, 1990; and Ausubel, F. M. et al., eds., 1989, Current Protocols in Molecular Biology, vol. 1, Green Publishing Associates, Inc., and John Wiley & Sons, Inc., NY. If desired, xylanase may be isolated using the PCR "RACE" technique, or Rapid Amplification of cDNA Ends (see, e.g., Innis et al.,.) By this method, oligonucleotide primers based on a xylanase conserved domain are oriented in the 3' and 5' directions and are used to generate overlapping PCR fragments. These overlapping 3'-and 5'-end RACE products are combined to produce an intact full-length cDNA.

An additional use for xylanase probes involves their use as oligonucleotide primers for PCR, the polymerase chain reaction. Such PCR materials can be provided in the form of a kit. The kit may include all of the components necessary for carrying out the PCR analysis. Such components may include one or more oligonucleotide primers, PCR reaction buffer, DNA polymerase enzyme, gel electrophoresis analysis materials, directions for carrying out the PCR reactions, and the like. The polymerase chain reaction is described in detail in U.S. Pat. Nos. 4,965,188 and 4,683,195 and 4,800, 195 which are hereby incorporated by reference. PCR techniques allow for the production of relatively large amounts of DNA for analysis of gene sequences, gene expression, etc. from small amounts of DNA.

Probes for hybridization may be synthesized by both enzymatic and in vitro techniques. Short hybridization probes are preferably synthesized by in vitro methodology such as the use of commercially available DNA synthesizers like machines sold by Applied Biosystems (Foster City, Calif.). For example, nucleotide sequences of lengths greater than 10 base pairs may be produced by commercially available machines. Oligonucleotides produced by in vitro synthesis may be readily spliced together using generally known recombinant DNA techniques to produce a longer sequence of interest.

Other means of producing xylanase-specific hybridization probes include the cloning of nucleic acid sequences encoding xylanase derivatives into vectors for the production of RNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

It is also possible to produce a DNA sequence, or portions thereof, encoding xylanase or xylanase derivatives entirely by synthetic chemistry, after which the gene can be inserted into any of the many available DNA vectors using reagents, vectors and cells that are freely available and in the public domain at the time of the filing of this application. Synthetic chemistry may be used to reproduce the entire sequence of a xylanase encoding gene, any portion thereof, or to introduce mutations into the sequence.

Nucleotide sequences encoding xylanase sequence may be used to produce purified xylanase protein or peptides using well-known methods of recombinant DNA technology. Among the many publications that teach methods for the expression of genes after they have been isolated is *Gene Expression Technology, Methods and Enzymology*. Vol.:185, edited by Goeddel, Academic Press, San Diego, Calif. (1990). Xylanase proteins or peptides may be expressed in a variety of host cells, or insert cells either prokaryotic or eukaryotic. Such cells can be microbial, mammalian, avian or plant cells. Preferably, host cells would be eukaryotic, more preferably host cells would be plant, most preferably host cells would be dicot cells. Host cells may be from species either the same or different than the species from which the xylanase encoding nucleotide sequences are naturally present, i.e., endogenous.

Once identified, xylanase genes can be expressed in a variety of cells including plant cells, yeast cells, fungi cells, bacterial cells and mammalian cells. A wide variety of plants can be transformed to express xylanase genes and genes related to xylanase in order to regulate plant fruit ripening.

Methods for transforming a wide variety of different dicots and obtaining transgenic plants are well documented in the literature (See Gasser and Fraley (1989) *Science* 244:1293; Fisk and Dandekar (1993) *Scientia Horticulturae* 55:5–36; Christou (1994) *Agro Food Industry Hi Tech* (March/April 1994) p. 17, and the references cited therein). A detailed protocol for transforming papaya is outlined in the Example section below.

Methods for producing transgenic plants among the monocots are currently available and known to those of skill in the art.

A variety of expression vectors can be used to transfer a gene encoding plant xylanase activity as well as the desired promoters and regulatory proteins into a plant. Examples include but not limited to those derived from a Ti plasmid of *Agrobactelium tumefaciens*, as well as those disclosed by Herrera-Estrella, L., et al., Nature 303: 209 (1983), Bevan, M., Nucl. Acids Res. 12: 8711–8721 (1984), Klee, H. J., Bio/Technology 3: 637–642 (1985), and EPO Publication 120,516 (Schilperoort et al.) for dicotyledonous plants and monocotyleclonous plants (M. Uze, et al. Plant Science 130:87 (1997). Alternatively, non-Ti vectors can be used to transfer the DNA constructs of this invention into monotyledonous plants and plant cells by using free DNA delivery techniques. Such methods may involve, for example, the use of liposomes, electroporation, microprojectile bombardment, silicon carbide wiskers, viruses and pollen. By using these methods transgenic plants such as wheat, rice (Christou, P., Bio/Technology 9: 957–962 (1991)) and corn (Gordon-Kamm, W., Plant Cell 2: 603–618 (1990)) are produced.

After transformation of cells or protoplasts, the choice of methods for regenerating fertile plants is not particularly important. Suitable protocols are available for Leguminosae (alfalfa, soybean, clover, etc.), Umbelliferae (Carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops See protocols described in Ammirato et al. (1984) *Handbook of Plant Cell Culture Crop Species*. Macmillan Publ. Co.; Shimamoto et al. (1989) Nature 338:274–276; Fromm et al. (1990) *Bio/Technology* 8:833–839; Vasil et al. (1990) Bio/Technology 8:429–434.

Cells transformed with expression vectors encoding xylanase proteins may be cultured under conditions favoring expression of the xylanase sequence and the recovery of the recombinantly-produced protein from the cell culture. A xylanase produced by a recombinant cell may be secreted or may be contained intracellularly, depending on the particular genetic construction used. In general, it is more convenient to prepare recombinant proteins in secreted form. Purification steps will depend on the nature of the particular xylanase produced.

Advantages of producing the xylanase proteins or peptides by recombinant DNA technology include obtaining highly enriched sources of the proteins for purification and the availability of simplified purification procedures that permit rapid purification of large amounts of the protein.

In addition to recombinant production, xylanase protein fragments may be produced by direct peptide synthesis using solid-phase techniques.

In vitro polypeptide synthesis may be performed using manual techniques or by automation. Automated synthesis may be achieved, for example, using Applied Biosystems 431A Peptide Synthesizer (Foster City, Calif.) following the instructions provided in the instruction manual supplied by the manufacturer.

Antibodies specific for xylanase proteins and peptides may be produced using purified xylanase protein or peptides for the induction of xylanase-specific antibodies. By induction of antibodies it is intended not only the stimulation of an immune response by injection into animals, but analogous steps in the production of synthetic antibodies or other specific-binding molecules such as the screening of recombinant immunoglobulin libraries. Both monoclonal and polyclonal antibodies can be produced by procedures well known in the art.

The examples below are provided to illustrate the subject invention. These examples are provided by way of illustration and are not included for the purpose of limiting the invention.

EXAMPLES

Example 1

Xylanase Extraction Protocol

Extraction: Ripe papaya (Carica papaya L.) mesocarp (cv. Sunset, Line 8) was homogenized in 2 vol of 50 mM sodium phosphate buffer (pH 4.5) and 1 mM 2,2'-dithiodipyridine (Sigma) in blender for 2 min at medium speed. The homogenate was centrifuged at 20,000 g for 15 min, and the supernatant filtered through 2 layers of Miracloth (Calbiochem). The filtrate was concentrated through an Amicon concentrator (100,000 molecular weight Cutoff) and the concentrated supernatant containing mainly pectin and molecules larger than ca. 100 kD was discarded. The filtrated solution was further concentrated through an cartridge cutoff 30 kD to remove low molecular weight proteins including papain.

Purification: Concentrated extract was loaded onto a S-Sepharose column (55×90 mm, Pharmacia) equilibrated with 50 mM sodium phosphate buffer (pH 4.5) and the proteins eluted with 1 M NaCl in phosphate buffer. The eluted xylanase active fractions were concentrated and dialysed against phosphate buffer (pH 4.5). The pellet was removed by centrifugation and the supernatant applied to a small S-Sepharose column (10×10 mm) in sodium phosphate buffer (pH 4.5). The column was eluted with a salt gradient (0 to 0.3M NaCl) in 50 mM phosphate buffer.(pH 4.5).

All xylanase active fractions were pooled, concentrated and applied to a Phenyl Superose HR 5/5 column (Pharmacia) equilibrated with 1.7 M $(NH_4)SO_4$ in 50 mM sodium phosphate buffer (pH 7). Samples were eluted with a linear gradient of $(NH_4)_2SO_4$ from 1.7 M to 0 M in sodium phosphate buffer (pH 7.0). All active fractions were again pooled and loaded onto a Mono-S HR 5/5 column (Pharmacia) in 50 mM sodium acetate buffer (pH 4.6). A step gradient of NaCl from 0 to 120 mM in sodium acetate buffer (pH 4.6) were used to eluted proteins. Active fractions were combined, concentrated and applied to a Superdex 75 column (Pharmcia) equilibrated with 50 mM sodium phosphate buffer, (pH 7), and 150 mM NaCl. Proteins were eluted with same buffer. This xylanase was used for determining substrate specificity and characteristics.

Example 2

Enzyme Assays

Cellulase: Carboxy methyl cellulose (NBC) 0.4 ml (1% WN) in 50 mM sodium-acetate buffer (pH 6.7) and 0.04 ml enzyme were incubated at 37° C., with 0.25% (W/V) β-lactoglobulin. The flow rates of the reaction mixtures in a modified 0.1 ml pipet were measure. Cellulase activity was calculated by the relative change in flow rates after incubation (Paull and Chen, 1983).

Pectin Methyl Esterase: Reaction mixtures of 5 ml of 0.5% polygalacturonic acid methyl ester (Sigma) pH 7.5 and 0.04 ml enzyme were incubated at 22° C., with 0.25% β-lactoglobulin. Activities were measured as the amount of NaOH necessary to maintain the reaction mixture at pH 7.5, over a fixed time period.

Polygalacturonase: Polygalacturonic acid (Sigma) 500 µl 0.45% (w/v) in 50 mM Na-acetate buffer (pH 5) 500 µl, 10 µl enzyme and 2 µg β-lactoglobulin were incubated at 37° C. Reaction was terminated by the addition of 1 ml of 0.1% (w/v) cyanoacetomide in 100 mM borate buffer (pH 9.0) and boiled for 10 min (Gross, 1982). Activity was calculated as galacturonic acid released.

Xylanase: Xylanase activity was routinely determined by the release of Remazol dye from water soluble xylan (Biely et al., 1985). The substrates (0.4 ml 0.1% 4-O-methyl-d-glucurono-D-xylan-Remazol brilliant blue R (Sigma)) in 50 mM sodium acetate buffer (pH 5.0) was incubated with enzyme aliquots at 37° C., with or without 100 µg β-lactoglobulin. The reaction was terminated by the addition of 1 ml ethanol (95%), mixed and pelleted at 8,000 g for 5 min after 30 min. Enzyme activities were reported as the absorption at 595 mm.

Larch wood and birch wood xylans (Sigma) 500 µL (0.7% w/v) in 50 mM Na-acetate buffer (pH 5.0) was mixed with 10 µL of enzyme and 2 µg of β lactoglobulin and incubated at 40° C. Reactions were terminated by the addition 1 ml of 0.1% (w/v) cyanoacetomide in 100 mM borate buffer (pH 9.0) and assayed for reducing sugar (Gross, 1982). Enzyme activity was calculated based on amount of reducing sugar released.

Nitrophenyl-β-d-xylopyranosidase. The assay mixture contained 0.5 ml 12 mM nitrophenyl-β-d-xylopyranoside (Sigma) in 50 mM Pipes buffer (pH 6.5) 50 µM succinic acid, 100 µg β-lactoglobulin and 10 µl enzyme. The mixture was incubated at 40° C. for 4 hr and terminated by the addition of 1 ml 1 M $Na_2CO_3$. Enzyme activity was calculated based on the release of β nitrophenyl substrate measured at 405 nm.

OBR-hydroxy ethylcellulose. The assay mixture contained 0.35 ml 0.1% (w/v) OBR-hydroxy ethyl-cellulose (Sigma) in 50 mM Pipes buffer (pH 6.5), endo-1,4-β-glucan, 100 µg β-lactoglobulin and 20 µl enzyme and incubated at 40° C. The reaction was terminated by the addition of 1.2 ml of a (2:1) mixture of ethanol and acetone and solution measured at 550 nm.

Temperature andpH Optimum: Aliquots of purified enzyme (40 µL) were incubated with 0.4 ml of 0.1% (w/v) RBB xylan (Sigma) in 50 mM sodium acetate (pH 5.0) buffer with 100 µg β-lactoglobulin (Sigma) for 4 hours. The enzyme activity was determined by terminating the reaction by the addition of 1 ml of ethanol (95% v/v) and mixed. The mixture was pelleted at 8,000×g for 5 min after standing for 5 min. Enzyme activity was reported as the absorption at 595 nm. The effect of pH on activity was measured by incubating 40 µl enzyme at 37° C. at different pH for 4 hr.

Xylanase Enzyme activity and Cations: The effect of different cations on the enzyme activity was tested by incorporating 10 mM of different cations in a xylanase reaction mixture in sodium phosphate buffer (pH 6.5) and incubate at 40° C. for 4 hr. The reaction was terminated with 1 ml of ethanol (95%) and absorption measured at 595 nm.

Substrate specificity of the partially purified xylanase protein from Example 1 is shown in Table 1.

TABLE 1

Substrate specificity of the partially purified xylanase prior to separation on polyacrylamide gel.

| Substrate | Activity after 4 hour incubation ug glucose • hr$^{-1}$ |
| --- | --- |
| Pectin | 0 |
| Polygalacturonic acid | 0.75 |
| CM Cellulose | 0 |
| OBR-hydroxy ethyl cellulose | 0 |
| Nitrophenyl-β-xylopyranoside | 0 |
| RBB-xylan | 6.7 |

Example 3

Xylanase Purification:

All fractions (0.5 ml) eluted from the Superdex 75 column (Example 1) were assayed for xylanase activity (Example 2) and active fractions were independently concentrated to less than 50 µl. Concentrated protein samples were denatured and run on a SDS page gel. The xylanase protein was identified based on the relationship between enzymatic activity and protein band pattern changes and determined to be a 32.5 kD protein.

After the xylanase band identification, a large scale preparation using 10 kg of papaya mesocarp was carried followed the procedure described above. All active fractions from the Superdex 75 column were then pooled and concentrated to produce maximum protein yield. The pooled protein fractions were run on an SDS PAGE gel and the xylanase 32.5 kD protein band was cut out, rinsed with Milli-Q water and stored in micro-centrifuge vial. Excess water was removed before storage at −20° C.

Example 4
Protein Sequencing

Protein samples from Example 3 were sent to the Stanford University Protein and Nucleic Acid Facility for amino acid sequencing. Amino acid sequencing was carried out on HPLC fraction following trypsin digestion. Five usable peptide sequences that ranged from 10 to 27 amino acids in length were obtained. Amino acid sequences showed high homology to endo-1,4-Beta Xylanase isolated from Hordeum vulgare and a number of microorganisms (see Table 2). Four peptide sequences were identified. The sequences presented start at the carboxy terminus:

1. KNGIAIRGHNVFWDDPK SEQ ID NO: 1
2. RINSVMNRYKGQVIGWDWNENLHFSFFESK SEQ ID NO: 2
3. TDPSTTLFMNEYNTVEDSRDGQATPAK SEQ ID NO: 3
4. LRSIQSLPGNGNMGIGLESHFS SEQ ID NO: 4

Example 5
RNA Isolation and Library Construction

Total RNA was isolated following a modification of the procedure of Lopez-Gomez and Gomez-Lim (1992). Papaya mesocarp from fruit that had started to soften (ca 50% to 80% yellow) were used. Fruit were cut in half and the seeds removed. The skin was removed and mesocarp was cut into small pieces and immediately frozen in liquid nitrogen. The frozen tissue was ground to a powder in the presence of liquid nitrogen and extracted with 2 volumes of extraction buffer (150 mM Tris base, 2% (w/v) SDS, 50 mM EDTA, 1% (V/V) B-mercaptoethanol, adjusted to pH 7.5 with boric acid) for 1 min at room temperature. One volume of hot phenol (equilibrate to pH 7 with 0.1M Tris) was added and the extracted tissue was mixed vigorously for 1 min. After this step, 0.25 volumes of ethanol and 0.11 volumes of 5 M potassium acetate were added and the mixture was stirred for another minute. One volume of chloroform was added to the homogenate and stirred the mixture was stirred for 1 min before centrifugation at 23,000 g for 20 min. The recovered aqueous phase was extracted with one volume of Phenol:chloroform until no interphase was present. The aqueous phase was then extracted with 2 volumes of chloroform. RNA in aqueous phase was precipitated with LiCl by adding a sufficient amount to make the final concentration 2.5 Molar. After standing overnight at −20° C., RNA was pelleted by centrifuged at 23,000 g for 90 min at 4° C. The pellet was washed twice with 2.5 M LiCL and resuspended in RNase free water. Two and half volumes of 100% ethanol and 0.1 volumes of 3 M sodium acetate were added and stored at −20° C. overnight. The RNA solution was centrifuged at 14,000 g for 30 min. The RNA pellet was washed twice with 70% ethanol, vacuum dried and resuspended in Rnase free water.

Promega's PolyATtract mRNA isolation kit was used to isolate mRNA from the total RNA. Three mg of total RNA yielded 15 µg of mRNA. Seven µg of mRNA was used to construct cDNA library using a Stratagene Uni-ZAP XR Cloning kit. The library constructed had a titer of $10^{-9}$ pfu/ml.

Example 6
cDNA Isolation

First strand cDNA was synthesized by heating 1 µg of Poly(A)+ RNA with 1 µl of Oligo(dT) (0.5 µg/µl) at 70° C. for 10 min. and quenched on ice for at least 1 min. Two µl of 10×PCR buffer (200 mM Tris-HCl pH 8.4, 500 mM KCl), 2 µl of 25 mM $MgCl_2$, 1 µl of 10 mM dNTP mixture and 2 µl of 0.1M DTT. The reaction mixture was incubated at 42° C. for 5 min before adding 1 (200 units) of SuperScript II RT (GIBCO BRL Life Technologies) and incubated at 42° C. for 50 min. The reaction was terminated by heating at 70° C. for 15 min and stored on ice.

Thirteen degenerate oligonucleotide primers were designed based on the amino acid sequence of purified papaya xylanase and synthesized initially to isolate the xylanase gene. RT PCR was performed in a reaction mixture of 10 mM Tris-HCl, pH 9.0, containing 50 mM KCl, 1.5 mM $MgCl_2$ and 0.1% Triton x-100, 2.5 mM dNTP and 1.0 unit Taq DNA polymerase. One microgram of first strand cDNA was used as template and two 20 µM of degenerate primers used in a total volume of 25 µl. The PCR parameters were 1 min template denaturation at 95° C., 1 min primer annealing at 52° C. and 1 min primer extension at 72° C. for 35 cycles plus a final extension at 72° C. for 7 min. The products of PCR reaction were analyzed on a 1% agarose gels. A 280 bp DNA was replicated when Xyl-20 and Xyl-21 were used as primers. DNA was cut out the gel and eluted. The elute fragment was sequenced and 2 gene specific oligonucleotide primers Xyl-31 and Xyl-32 were synthesized.

A longer DNA fragment, ca. 850 bp was synthesized using Xyl-31 and oligo (dT) 37mer as primers and cDNA library as template. The 850 bp DNA was labeled with Digoxigenin-11-dUTP using a random primed method (DIG system, Boehringer Mannheim Biochemicals) and used as the probe to screen cDNA library. The cDNA library was screened using DIG system (Boehringer Mannheim Biochemicals).

The degenerate primer sequences used were:

| Primer No. | Sequence | SEQ ID NO |
|---|---|---|
| Xyl-11 | 5'-CAWGTNATHGGNTGGAYGT-3' | 5 |
| Xyl-12 | 5'-TGGGAYGTNGTNAAYGAWAA-3' | 6 |
| Xyl-13 | 5'-CAYAAYGTNTTYTGGGAYGAYCC-3' | 7 |
| Xyl-14 | 5'-ACWTCCCANCCDATNACYTG-3' | 8 |
| Xyl-15 | 5'-TTYTCWTTNACNACWTCCCA-3' | 9 |
| Xyl-16 | 5'-GGWTCWTCCCAWAANACWTTWTG-3' | 10 |
| Xyl-17 | 5'-TTYATGAAYGAWTAYAAYACNGT-3' | 11 |
| Xyl-18 | 5'-AAYGGNAAYATGGGNATHGG-3' | 12 |
| Xyl-19 | 5'-CCDATNCCCATWTTNCCWTT-3' | 13 |
| Xyl-20 | 5'-ACNGTVVTTRTAYTCWTTCATWAA-3' | 14 |
| Xyl-21 | 5'-GGNCAYAAYGTITTYTGGG-3' | 15 |
| Xyl-22 | 5'-GGNATGAAYAAGITATAAWGG-3' | 16 |
| Xyl-23 | 5'-CCDATICCCATWTTICCWTTNCC-3' | 17 |

MIXED BASES: W:A/T Y:C/T H:/A/C/T D:A/G/T N:A/C/G/T
I: inosine

The sequence of gene specific oligonucleotide primers were:

| Primer No. | Sequence | SEQ ID NO |
|---|---|---|
| Xyl-31 | 5'-TGGCGAAGCTCATAAGACTG-3' | 18 |
| Xyl-32 | 5'-GTTGTTGATGGATCAGTCTT-3' | 19 |
| Xyl-41 | 5'-CGAAGTATCAATCAGGATGG-3' | 20 |
| Xyl-42 | 5'-GGTTGGTAAGTTGTGGAAGT-3' | 21 |

-continued

| Primer No. | Sequence | SEQ ID NO |
|---|---|---|
| Xyl-43 | 5'-ATGGAAGAGTGAGCTCTGAA-3' | 22 |
| Xyl-44 | 5'-CCAACCAATAACTTGACCTT-3' | 23 |

A full length clone was isolated and sequenced. The cDNA sequence is shown in SEQ ID NO: 24. The corresponding peptide sequence is presented in SEQ ID NO: PATENT 25. This sequence also shows homology with 1,4-beta-xylanase-like or putative proteins found in Arabidopsis (see Table 2).

TABLE 2

Amino acid sequence homology of the papaya xylanase clone compared with other reported sequences.

| Number | Species and Description | | Identity |
|---|---|---|---|
| AL031032 | Arabidopsis thaliana | Putative protein | 59% |
| AL031394 | Arabidopsis thaliana | Xylan endohydrolase-like protein | 46% |
| AC005387 | Arabidopsis thaliana | Hypothetical Protein | 46% |
| AC004122 | Arabidopsis thaliana | Similar to endo xylanase | 30% |
| U59313 | Hordeum vulgare | β-1,4-xylan endohydrolase | 37% |
| U73749 | Hordeum vulgare | β-1,4-xylan endohydrolase | 33% |
| U41627 | Streptomyces halstedii | Xylanase | 28% |
| JC5034 | Emericella nidulans | Xylanase | 28% |

The homology between the Arabidopsis putative protein and the papaya xylanase sequences is high (59%), though the role of these Arabidopsis xylanase like sequences are unknown. The number of different Arabidopsis sequences suggests at least three or four different xylanase genes may exist. There was less homology between our clone and the barley sequences (37% and 33%). The barley xylanase may only play a role in aleurone wall degradation (Slade et al., 1989) and not growth, as no mRNA transcripts are detected in young vegetative tissue (Banik et al., 1996). There is conserved sequence homology with bacterial and fungal sequences, however, overall homology is less than 30% (see Table 3). Micro-organisms have been shown to have multiplicity of xylanases (Wong et al., 1988; Sunna and Antranikian, 1997).

Example 7

Identification and Isolation of Xylanases From Other Plants

The unique nature of the papaya xylanase allow its use as a tool for identifying other xylanases. Other xylanases may be identified by comparing the cloned sequence to sequences available in various databases. Substantially identical sequences are presented in Table 3.

TABLE 3

Muitiple Sequence Alignment Results
Papaya clone #8

```
MSF: 1143 Type: P May 6, 1999 17:12 Check: 3180 Gap Weight: 8
Gap Length Weight: 2

Name: aac45554   Streptomyces      Len: 1143  Check: 6146 Weight: 1.00
            (SEQ ID NO: 26)
            Name: baa75475   Aspergillus       Len: 1143  Check: 4949 Weight: 1.00
            (SEQ ID NO: 27)
            Name: aab38389   Barley 7          Len: 1143  Check: 6307 Weight: 1.00
            (SEQ ID NO: 28)
            Name: aac34334   Similar to        Len: 1143  Check: 9308 Weight: 1.00
            (SEQ ID NO: 29) xylanase
            Name: caa19864   Putative protein  Len: 1143  Check: 1221 Weight: 1.00
            (SEQ ID NO: 30)
            Name: caa20594   Putative protein  Len: 1143  Check: 7245 Weight: 1.00
            (SEQ ID NO: 31)
            Name: Papaclone8 Papaya xylanase   Len: 1143  Check: 3430 Weight: 1.00
            (SEQ ID NO: 25)
            Name: caa19866   Putative protein  Len: 1143  Check: 6643 Weight: 1.00
            (SEQ ID NO: 32)
            Name: aac77919   Zea mays          Len: 1143  Check: 7931 Weight: 1.00
            (SEQ ID NO: 33)
                        1                                                      50
             aaac4554   ----------  ----------  ----------  ----------  ----------
             baa75475   ----------  ----------  ----------  ----------  ----------
             aab38389   ----------  ----------  ----------  ----------  ----------
             aac34334   MADLNIVMNG  DFFAGIEPWY  PNGCEAFVVS  SDPFSSEVMS  ADSSSGGYVV
             caa19864   ----------  ----------  ----------  ----------  ----------
             caa20594   ----------  ----------  ----------  ----------  ----------
           Papaclone8   ----------  ----------  ----------  ----------  ----------
             caa19866   ----------  ----------  ----------  ----------  ----------
             aac77919   ----------  ----------  ----------  ----------  ----------

51                                                     100
             aac45554   ----------  ----------  ----------  ----------  ----------
             baa75475   ----------  ----------  ----------  ----------  ----------
             aab38389   ----------  ----------  ----------  ----------  ----------
             aac34334   VTNRKETWQG  LEQDITTRVA  SGMNYTVSTC  VGVSGPFNES  AEVLSTVRLE
```

TABLE 3-continued

Multiple Sequence Alignment Results
Papaya clone #8

MSF: 1143 Type: P May 6, 1999 17:12 Check: 3180 Gap Weight: 8
Gap Length Weight: 2

```
      caa19864   ---------- ---------- ---------- ---------- ----------
      caa20594   ---------- ---------- ---------- ---------- ----------
   Papaclone8   ---------- ---------- ---------- ---------- ----------
      caa19866   ---------- ---------- ---------- ---------- ----------
      aac77919   ---------- ---------- ---------- ---------- ----------

101                                                 150
      aac45554   ---------- ---------- ---------- ---------- ----------
      baa75475   ---------- ---------- ---------- ---------- ----------
      aab38389   ---------- ---------- ---------- ---------- ----------
      aac34334   HEDSPTEYLC IGKTYASRDK WVDLEGTFSI SNMPDRVVLY LEGPAPGKDL
      caa19864   ---------- ---------- ---------- ---------- ----------
      caa20594   ---------- ---------- ---------- ---------- ----------
   Papaclone8   ---------- ---------- ---------- ---------- ----------
      caa19866   ---------- ---------- ---------- ---------- ----------
      aac77919   ---------- ---------- ---------- ---------- ----------

151                                                 200
      aac45554   ---------- ---------- ---------- ---------- ----------
      baa75475   ---------- ---------- ---------- ---------- ----------
      aab38389   ---------- ---------- ---------- ---------- ----------
      aac34334   LIRSVTVRSS TSSDFQETEK NTDASNVFPL ALNIIKNHDF SDGLYSWNTN
      caa19864   ---------- ---------- ---------- ---------- ----------
      caa20594   ---------- ---------- ---------- ---------- ----------
   Papaclonea   ---------- ---------- ---------- ---------- ----------
      caa19866   ---------- ---------- ---------- ---------- ----------
      aac77919   ---------- ---------- ---------- ---------- ----------

201                                                 250
      aac45554   ---------- ---------- ---------- ---------- ----------
      baa75475   ---------- ---------- ---------- ---------- ----------
      aab38389   ---------- ---------- ---------- ---------- ----------
      aac34334   GCDSFVVSSN DCNLESNAVV NNRSETWQGL EQDITDNVSP GFSYKVSASV
      caa19864   ---------- ---------- ---------- ---------- ----------
      caa20594   ---------- ---------- ---------- ---------- ----------
   Papaclone8   ---------- ---------- ---------- ---------- ----------
      caa19866   ---------- ---------- ---------- ---------- ----------
      aac77919   ---------- ---------- ---------- ---------- ----------

251                                                 300
      aac45554   ---------- ---------- ---------- ---------- ----------
      baa75475   ---------- ---------- ---------- ---------- ----------
      aab38389   ---------- ---------- ---------- ---------- ----------
      aac34334   SVSGPVLGSA QVLATLKLEH KSSATEFQLI GKTYASKDIW KTLEGTFEVS
      caa19864   ---------- ---------- ---------- ---------- ----------
      caa20594   ---------- ---------- ---------- ---------- ----------
   Papaclone8   ---------- ---------- ---------- ---------- ----------
      caa19866   ---------- ---------- ---------- ---------- ----------
      aac77919   ---------- ---------- ---------- ---------- ----------

301                                                 350
      aac45554   ---------- ---------- ---------- ---------- ----------
      baa75475   ---------- ---------- ---------- ---------- ----------
      aab38389   ---------- ---------- ---------- ---------- ----------
      aac34334   GRPDRVVFFL EGPPPGIDLL VKSVTIHCES DNQFERSREF CSAPESDNHI
      caa19864   ---------- ---------- ---------- ---------- ----------
      caa20594   ---------- ---------- ---------- ---------- ----------
   Papaclone8   ---------- ---------- ---------- ---------- ----------
      caa19866   ---------- ---------- ---------- ---------- ----------
      aac77919   ---------- ---------- ---------- ---------- ----------

351                                                 400
      aac45554   ---------- ---------- ---------- ---------- ----------
      baa75475   ---------- ---------- ---------- ---------- ----------
      aab38389   ---------- ---------- ---------- ---------- ----------
      aac34334   FLNSSFSDGL NHWSGRGCNL MLHESLADGK ILPDSGTCFA SASERTHKWS
      caa19864   ---------- ---------- ---------- ---------- ----------
      caa20594   ---------- ---------- ---------- ---------- ----------
   Papaclone8   ---------- ---------- ---------- ---------- ----------
      caa19866   ---------- ---------- ---------- --MLKELQSI RISGYIRLAI
      aac77919   ---------- ---------- ---------- ---------- ----------

401                                                 450
```

TABLE 3-continued

Multiple Sequence Alignment Results
Papaya clone #8

MSF: 1143 Type: P May 6, 1999 17:12 Check: 3180 Gap Weight: 8
Gap Length Weight: 2

```
     aac45554   ---------- ---------- ---------- ---------- ----------
     baa75475   ---------- ---------- ---------- ---------- ----------
     aab38389   ---------- ---------- ---------- ---------- ----------
     aac34334   GIEQDITERV QRKLIYEASS VVRLSHSHHT VQATLYVQYL DQREEYIGIS
     caa19864   ---------- ---------- ---------- ---------- ----------
     caa20594   ---------- ---------- ---------- ---------- ----------
   Papaclone8   ---------- ---------- ---------- ---------- ----------
     caa19866   GLESHFKTPN IPYMRSALDI LAATGLLIWL TEIDVEAPPS VQAKYFEQVL
     aac77919   ---------- ---------- ---------- ---------- ----------

451                                                500
     aac45554   ---------- ---------- ---------- ---------- ----------
     baa75475   ---------- ---------- ---------- ---------- ----------
     aab38389   ---------- ---------- ---------- ---------- ----------
     aac34334   SVQGTHDDWV ELKGKFLLNG SPARAVVYIE GPPPGIDVFV DHFAVKPAEK
     caa19864   ---------- ---------- ---------- ---------- ----------
     caa20594   ---------- ---------- ---------- ---------- ----------
   Papaclone8   ---------- ---------- -----MKLGE KNLQFYFLLV LPYALLFPGL
     caa19866   RDGHAHPQVK GMVVWGGYSP SGCYRMCLTD GNFR.....N LPTGDVWTCC
     aac77919   ---------- ---------- ---------- ---------- ----------

501                                                550
     aac45554   ---------- ---------- ---------- ---------- ----------
     baa75475   ---------- ---------- ---------- ---------- ----------
     aab38389   ---------- ---------- ---------- ---------- ----------
     aac34334   ETPSGRPYIE SHAFGMNIVS NSHLSDGTIE GWFPLGDCHL KVGDGSPRIL
     caa19864   ---------- ---------- ---------- ----MKPPRS SETKGLLQFS
     caa20594   ---------- ---------- ---------- ----MKPPRS SETKGLLQFS
   Papaclone8   ETNALSYDYT ASIQCLENPQ KAQYGGGIIT NPELNQGLKG WSTFGDAKIQ
     caa19866   YVN..GEDFA AKQQCLENPY KPQYNGGIIV NPDLQNGSQG WSQFGNAKVD
     aac77919   ---------- ---------- ---------- ---------- ----------

551                                                600
     aac45554   ---------- ---------- ---------- ---------- ----------
     baa75475   ---------- ---------- ---------- ---------- ----------
     aab38389   ---------- ---------- ---------- ---------- ----------
     aac34334   PPLARDSLRK TQGYLSGRYV LATNRSGTWM GPAQTITDKV KLFVTYQVSA
     caa19864   RSLEDDSDEE WKIDGNGFIR EMAQRIQLHQ GNIYSFSAWV KLREGNDRKV
     caa20594   RSVEDDSDEE WKIDGSGSIR EMTQRIQLHE GNIYSFSAWV KLREGNNKKV
   Papaclone8   HRVAGSNSFI VAHTRSQPHD SVSQTLYLQS NKLYTFSAWI RVSEGKTP.V
     caa19866   FREFGGNKFV VATQRNQSSD SISQKVYLEK GILYTFSAWL QVSIGKSP.V
     aac77919   ---------- ---------- ---------- ---------- ----------

601                                                650
     aac45554   ---------- ---------- ---------- ---------- ----------
     baa75475   ---------- ---------- ---------- ---------- ----------
     aab38389   ---------- ---------- ---------- ---------- --MGAFRLRT
     aac34334   WVKIGS.GGR TSPQDVNIAL SVDGNWVNGG KVEVDDGDWH EVVGSFRIEK
     caa19864   GVVFRTENGR LVHGGEVAAN QECWTLLKGG IVPDFSGPVD IFFEIHTYIL
     caa20594   GVVFRTENGR FVHGGEVRAK KRCWTLLKGG IVPDVSGSVD IFFEVQQLAI
   Papaclone8   KAIFKT.KSG YKYAGAVVAE SNCWSMLKGG LTVDASGPAE LYFE......
     caa19866   SAVFKK.NGE YKHAGSVVAE SKCWSMLKGG LTVDESGPAE LFFE......
     aac77919   ---------- ---------- ---------- ---------- ----------

651                                                700
     aac45554   ---------- ---------MA QNPPVGGRTR RRPQAAARCA LSLLTAGVLA
     baa75475   ---------- ---------- ---------- -------MVH LKALASGTLF
     aab38389   EPRSAAVVVH GAPAGVDVKV MDLRVYPVDH KARFRQLKDK TDKARKRDVI
     aac34334   EAKEVMLHVQ GPSPGVDLMV AGLQIFAVDR KARLSYLRGQ ADVVRKRNVC
     caa19864   CVNVVLMRKQ SENRGAKISA HNVLLKQFSK EEWKLKQDQL IEKIRKSKVR
     caa20594   .........Y SDDKEAKISA SDVSLKQFSK QEWKLKQDQL IEKIRKSKVR
   Papaclone8   .......... TDNTSVEIWI DSISLQPFTQ QEWKSHQDQS IKKIRKKVVR
     caa19866   .......... SENTMVEIWV DSVSLQPFTQ EEWNSHHEQS IGKVRKGTVR
     aac77919   ---------- ---------- ---------- ---------- ----------

701                                                750
     aac45554   AAGVVALAGT AQAAGALGDA AAAKG.RYFG AAVAANHLGE AAYASTLDAQ
     baa75475   ASLASSAVIS RQAAASINDA FVAHGKKYFG TCSDQALLQN SQNEAIVAAD
     aab38389   LKL.GTPAGA GAGAAASVRV VQLDNAFPFG TCINTSVIQK PAFLDFFTNH
     aac34334   LKFSGLDPSE LSGATVKIR. .QTRNSFPLG SCISRSNIDN EDFVDFFLNN
     caa19864   FEVTYENKTA VKGVVISLK. .QTKSSFLLG CGMNFRILQS QGYRKWFASR
     caa20594   FEVTYQNKTA VKGAVISIE. .QTKPSFLLG CAMNFRILQS EGYRNWFASR
   Papaclone8   IQAVDKLGNP LPNTTVSIS. .PKKIGFPFG CAINRNIVNN NAYQSWFSSR
```

TABLE 3-continued

Multiple Sequence Alignment Results
Papaya clone #8

MSF: 1143 Type: P May 6, 1999 17:12 Check: 3180 Gap Weight: 8
Gap Length Weight: 2

```
              caa19866    IRVMNNKGET  IPNATISIE.  .QKKLGYPFG  CAVENNILGN  QAYQNWFTQR
              aac77919    ---MGANDKP  MAHANVSIE.  .LLRLGFPFG  NAVTKEILGL  PAYEKWFTSR 751                                                     800
              aac4SSS4    FGSVTPENEM  KWDAVESSRN  SFSFSAADRI  VSHAQSKGMK  VRGHTLVWH.
              baa75475    FGQLTPENSM  KWDALEPSQG  SFSFAGADFL  ADYAKTNNKL  VRGHTLVNH.
              aab38389    FDWAVFENEL  KWYHTEVQQG  QLNYADADAL  LAFCDRLGKT  VRGHCVFWSV
              aac34334    FDWAVFGYEL  KWYWTEPEQG  NFNYRDANEM  IEFCERYNIK  TRGHCIFWEV
              caa19864    FKITSFTNEM  KWYATEKARG  QENYTVADSM  LKFAEDNGIL  VRGHTVLWDN
              caa20594    FKITSFTNEM  KWYTTEKERG  HENYTAADSM  LKFAEENGIL  VRGHTVLWDD
            Papaclone8    FTVTTFENEM  KWASTEPSQG  HEDYSTADAM  VQFAKKNGIA  IRGHNVFWDD
              caa19866    FTVTTFGNEM  KWYSTERIRG  QEDYSTADAM  LSFFKSHGIA  VRGHNVLWDD
              aac77919    FSVATFENEM  KWYSTEWTQN  HEDYRVPDAM  MSLMRKYKIK  VRGHNVFWDD 801                                                     850
              aac45554    .SQLPGWVSP  LAATD.LRSA  MNNHITQVMT  HYKGKIHSWD  VVNEAFQDGG
              baa75475    .SQLPSWVQG  ITDKDTLTEV  IKNHITTIMQ  RYKGQIYAWD  VVNEIFDE..
              aab38389    DGDVQQWVKN  L.NKDQLRSS  MQSRLEGLVS  RYAGRFKHYD  VVNE......
              aac34334    ESAIQPWVQQ  L.TGSKLEAA  VENRVTDLLT  RYNGKFRHYD  VNNE......
              caa19864    PKMQPSWVKN  IKDPNDVMNV  TLNRINSVMK  RYKGKLTGWD  VVNE......
              caa20594    PLMQPTWVPK  IEDPNDLMNV  TLNRINSVMT  RYKGKLTGWD  VVNE......
            Papaclone8    PKYQSGWVSS  L.SPNDLNAA  ATKRINSVMN  RYKGQVIGWD  VVNE......
              caa19866    PKYQPGWVNS  L.SGNDLYNA  VKRRVYSVVS  RYKGQLLGWD  VVNE......
              aac77919    QNSQMQWVKP  L.NLAQLKAA  MQKRLKSVVS  PYAGKVIHWD  VVNE......

851                                                     900
              aac45554    SGARRSSPFQ  DKLGNGFIEE  A.FRTARTVD  ADAKLCYNDY  NT......DG
              baa75475    DGTLRDSVFS  QVLGEDFVRI  A.FETAREAD  PNAKLYINDY  NL......DS
              aab38389    ..MLHGRFFR  DRLGDEDVPA  YMFKEVARLD  PEPVLFVNDY  N.VECGNDPN
              aac34334    ..MLHGSFYR  DRL.DSDARA  NMFKTAHELD  PLATLFLNEY  H.IEDGFDSR
              caa19864    ..NLHWDYFE  KMLG.ANAST  SFYNLAFKID  PDVRLFVNEY  NTIENTKEFT
              caa20594    ..NVHWDYFE  KMLG.ANASS  SFYNLAFKLD  PDVTMFVNEY  NTIENRVEVT
            Papaclone8    ..NLHFSFFE  SKLG.ANASA  VFYGEAHKTD  PSTTLFMNEY  NTVEDSRDGQ
              caa19866    ..NLHFSFFE  SKFG.PKASY  NTYTMAHAVD  PRTPMFMNEY  NTLEQPKDLT
              aac77919    ..NLHFNFFE  TKLG.PMASA  QIYQQVGQLD  RNAILFMNEF  NTLEQPGDPN 901                                                     950
              aac45554    QN.AKSNAVY  EMVKDFKQRG  VPIDCVGFQS  HFNSNSPVPS  DFQANLQRFA
              baa75475    ADYAKTKGMV  SYVKKWLDAG  VPIDGIGSQS  HYSANGFPVS  GAKGALTALA
              aab38389    ATPEKYAEQV  AWLQS...CG  AVVRGIGLQG  HVQNPVGEV.  .ICAALDRLA
              aac34334    SSPEKYIKLV  HKLQK...KG  APVGGIGIQG  HITSPVGHI.  .VRSALDKLS
              caa19864    ATPIKVKKMM  EEILAYPGNK  NMKGAIGAQG  HFGPTQPNLA  YIRSALDTLG
              caa20594    ATPVKVKEKM  EEILAYPGNM  NIKGAIGAQG  HFRPTQPNLA  YMRSALDTLG
            Papaclone8    ATPAKYLEKL  RSIQSL..PG  NGNMGIGLES  HFSSSPPNIP  YMRSAIDTLA
              caa19866    SSPARYLGKL  RELQSIRVAG  KIPLAIGLES  HFST..PNIP  YMRSALDTFG
              aac77919    PVPAKYVAKM  NQIRGYAGNG  GLKLGVGLES  HFST..PNIP  YMRSSLDTLA 951                                                     1000
              aac45554    DLGV.DVQIT  ELDIEGSGSA  QAANYTK.VV  NACLAVTRCT  GITVWGVTDK
              baa75475    STGVSEVAVT  ELDIEG...A  SSESYLE.VV  NACLDVSSCV  GITVWGFVSDK
              aab38389    KTGVP.TWFT  ELDVPEYDVG  LRAKDLEVVL  REAYAHPAVE  GIVFWGFMQG
              aac34334    TLGLP.IWFT  ELDVSSTNEH  IRGDDLEVML  WEAFAHPAVE  GVMLWGFWEL
              caa19864    SLGLP.IWLT  EVDMPKCP.N  .QAQYVEDIL  REAYSHPAVK  GIIIFGGPEV
              caa20594    SLGLP.IWLT  EVDMPKCP.N  .QEVYIEEIL  REAYSHPAVK  GIIIFAGPEV
            Papaclonee    ATGLP.VWLT  EVDVQSGG.L  .QAQSLEQIL  REAHSHPAVR  GIVIWSAWSP
              caa19866    ATGLP.IWLT  EIDVDAPP.N  VRANYFEQVL  REGHAHPKVN  GMVMWTGYSP
              aac77919    KLKLP.MWLT  EVDVVKSP.N  .QVKYLEQVL  REGFAHPNVD  GIVMWAGWHA 1001                                                    1050
              aac45554    YSWRSGGTPL  LFDGDYNKKP  AYDAVLAALG  GSGGGGDDGG  EGGDGACTAT
              baa75475    DSWRSSTSPL  LFDSNYQAKD  AYNAIIDAL-  ----------  ----------
              aab38389    TMWRQNAW..  LVDADGTVNE  AGQMFLNLQK  .....KTDAR  ......DGDG
              aac34334    FMSREHSS..  LVNADGEVNE  AGKRFLEIKR  EW...LSFVD  GEI...EDGG
              caa19864    SGFDKLT...  LADKDFNNTQ  TGDVIDKLLK  EWQQKSSEIQ  TNFTADSDNE
              caa20594    SGFDKLT...  LADKYFNNTA  TGDVIDKLLK  EWQQ.SSEIP  KIFMTDSEND
            Papaclone8    NGCYRMC...  LTDNNFHNLP  TGDVVDKLLR  EWGG.GATVK  ....KTDQNG
              caa19866    SGCYRMC...  LTDGNFKNLP  TGDVVDKLLR  EWGGLRSQTT  ....VTDANG
              aac77919    KGCYVMC...  LTNNSFKNLP  W..ATSSTSS  SPSGRRTARP  ....PPITMG 1051                                                    1100
              aac45554    YTRTSTWNGG  YNGQVTVKAG  GSGITGWAVP  VTVASPQKVS  AVWNGTPTTT
              baa75475    ----------  ----------  ----------  ----------  ----------
              aab38389    NFKFRGFYGR  YVVEVTTAKR  KQMLKTFTVE  KGDNTP..VV  VDLADA----
```

TABLE 3-continued

Muitiple Sequence Alignment Results
Papaya clone #8

MSF: 1143 Type: P May 6, 1999 17:12 Check: 3180 Gap Weight: 8
Gap Length Weight: 2

```
  aac34334    GLEFRGYHGS  YTVEVVTSES  K.YVTNFVVD  KG.NSPVDVI  IDL-------
  caa19864    EEEVSLLHGH  YVVN------  ----------  ----------  ----------
  caa20594    EEEVSLLHGH  YNVNVSHPWM  KNMSTSFSLE  VTKEMGQRQV  VRVVINA---
Papaclone8    FFQSSLFHGD  YEIKVQVNHP  SKLPSSSSHH  TFKLNSTDDE  S.KQTRLLLI
  caa19866    LFEAPLFHGD  YDLR..ISHP  ..LTNSKASY  NFTLTSDDDS  SQKQPSLYVF
  aac77919    RWSSTCP---  ----------  ----------  ----------  ----------

1101                                            1143
  aac45554    GDVMTVRHSW  NGTLAAGAST  TFGFTVQTNG  GTSAPVVGAC  TAS
  baa75475    ----------  ----------  ----------  ----------  ---
  aab38389    ----------  ----------  ----------  ----------  ---
  aac34334    ----------  ----------  ----------  ----------  ---
  caa19864    ----------  ----------  ----------  ----------  ---
  caa20594    ----------  ----------  ----------  ----------  ---
Papaclone8    KV--------  ----------  ----------  ----------  ---
  caa19866    RV--------  ----------  ----------  ----------  ---
  aac77919    ----------  ----------  ----------  ----------  ---
```

Example 8
Xylanase Antisense Expression in Transgenic Papaya

Both antisense suppression and co-supression have been used successfully in papaya. Antisense has been commonly used to down regulate wall degrading enzymes in other crops. Antisense expression of the papaya xylanase cDNA in papaya will be utilized to regulate xylanase expression and cell ripening.

The full length papaya cDNA clone (SEQ ID NO: 24) or fragments thereof are inserted behind the CaMV-35S or ubiquitin promoters and before the NOS 3' terminator sequences so that xylanase is in the anti-sense direction. Both the CaMV-35S and ubiquitin promoters are expressed in papaya.

The xylanase cDNA is in a Lambda ZAP library. The recovered cDNA inserted into the polylinker region of the XL1-Blue vector can then be attached to the CaMV 35S promoter and the NOS terminator sequence. Sequences are manipulated by standard recombinant DNA techniques (Sambrook et al., 1989) or by PCR using specific primers with appropriate restriction sites.

Many plasmids may be used for transforming papaya. The pGA 482 binary vector (An, 1986) contains left and right T-DNA borders, an NPT II gene for selection on kanamycin, tetracycline resistance gene for selection in bacteria and a polylinker region and is an example of a vector useful in the invention. If kanamycin is used for selection, the antisense xylanase construct (including the promoter and NOS terminator) will be inserted in the polylinker region. Disarmed Agrobacterium tumefaciens strain C58-Z707 (Hepburn et al., 1985) and AGLO (Lazo et al., 1991) containing the pGA 482 xylanase will be used. For bombardment, a simple vector consisting of the selectable marker and the antisense xylanase construct will be used.

Example 9
Transgenic Papaya

Transgenic papaya may be produced using procedures known in the art. Embryogenic zygotic embryos from 90 to 120 days old immature seeds of 'Line 8' and 'Sunset' papaya varieties are produced. The embryos are excised and plated onto induction media as previously described (Fitch et al., 1994) to produce calli. Extended periods of culture (6 to 8 months) in the presence of 2,4-D (induction media) prior to bombardment or co-cultivation with Agrobacterium is detrimental to regeneration (Fitch et al., 1993) and should be avoided. After excising the embryo, the calli are used within 3 months to avoid this regeneration problem. Bombardment and cocultivation with Agrobacterium have been successfully applied to the papaya embryonic tissue (Fitch et al., 1994) and bombardment used on somatic embryos (Cabrera-Ponce et al., 1995; Mahon et al., 1996).

For particle bombardment, embryos are cultured on sterile filter paper lying on the surface of a medium of 0.25 M mannitol and 0.8% agar to reduce turgor slightly, as developed by Perl et al., (1992), and applied to papaya Mahon el al., (1996) are utilized. The protocols for bombardment and cocultivation have been described Fitch et al., (1994).

Example 10
Identification of Transcenic Plants

GUS histochemical analysis is preformed three weeks after bombardment or cocultivation and at intervals thereafter for determination of transformation. Four months following transformation, the tissue growing on selection media can be assayed for GUS, (Jefferson, 1987) and NPT II (McDonnell et al., 1987). PCR preformed on extracted genomic DNA (Dellaporta et al., 1983) using NPR II and xylanase primers to amplify fragments of known size also can be used to assess transformation. The use of PCR will allow rapid screening of transgenics. Transformants showing proper antisense xylanase gene constructs are grown to a stage to allow Southern analysis (Sambrook et al., 1989) to confirm proper integration and the presence of specific sequences. Southern analysis helps to determine whether there is single or multiple loci insertion. Expression studies on extracted RNA, can be preformed on leaf tissue from untransformed and transgenic papaya. RNA extraction and Northern hybridization can be done as described by Fitch et al., (1994), and probed with xylanase primers.

Example 11
Analysis of Transgenic Plants

Transgenic plants are analyzed by enzyme assays, Northern analyses, antibody analysis, and tissue blotting.

A. Enzyme Assays

Endo-xylanase activity in transgenic plants are assayed using the chromogenic Remazol brilliant blue (RBB) xylan (Sigma), following the procedure of Biely et al., (1985) as described above in Example 2. Assays for other wall degrading enzymes will follow the procedures outlined by Paull and Chen (1983) and as described above. Xyloglucanase and XET activity, if required, can be determined using the procedures described by MacLachlan and Brady (1994) and as described above.

B. Northern Analysis

Intact RNA is extracted from fruit mesocarp using the procedure of Lopez-Gomez and Gomez-Lim (1992) as described above. RNAase protection assays are performed (Little and Jackson, 1987), with synthetized radiolabelled single stranded tissue RNA probes using a RNA transcription kit (Stratagene). Northern blots are performed by procedures well known in the art.

C. Antibody Preparation and Immunoblotting

Xylanase protection is purified as described in Example 1. Polyclonal antibodies to the purified protein will be produced by procedures well known in the art at a commercial laboratory. Alternatively, the xylanase can be overproduced in E. coli using a commercial kit (Stratagene) since about 1 mg of protein is required for antibody production. The use of E. coli will avoid protein glycolyslation and give greater antibody specificity to the xylanase protein and not the more antigenetic glycosyl groups. The E. coli recombinant xylanase will be purified on a charged column and the purity of selected fractions checked on SDS-PAGE.

Dot blots will be used to determine optimum antiserum concentration for Western blots. Antigen-antibody complexes will be developed with nitro blue tetrazolium using alkaline phosphatase-conjugated goat anti-rabbit IgC. Pre-immune rabbit serum will be the control. Protein blotting from SDS-PAGE gels and tissue blots will be preformed as required.

D. RNA Tissue Blotting and Immuno-cytohistochemistry

Spatial localization, tissue blotting and in situ staining will be tested on thin fruit slices, with sense and antisense RNA (McClure and Guilfoyle, 1989) and xylanase antibody (Tieman and Handa, 1989). The RBB-xylan immobilized in a thin agar layer as the blot media may be utilized as a tissue blot substrate (Mackenzie and Williams, 1984). Nitrocellulose membranes and immunocytochemical localization will also be utilized (Spruce et al., 1987). Tissue printing protocols have been devised and described in detail (Reid and Pont-Lezica, 1992). Protease inhibitors may be used to improve protein tissue blots. Latex exudation can be minimized by reducing latifer pressure by pre-sectioning prior to blotting. Alternatively, tissue will be fixed with formaldehyde, dehydrated and embedded in paraffin, then sectioned before immunocytohistochemistry.

Example 12

Assessment of Ripening, Quality Parameters

Transgenic papaya will be analyzed for ripening and quality parameters. Color of the skin of transgeneic papaya is measured with a Minolta Chromameter (CR-110) at three different equatorial sites. Firmness is measured with an 8 mm diameter probe connected to a digital force gauge depressed into four different areas of the flesh. Soluble sugars is measured by refractometry. Ethylene production is determined by GLC from headspace gas after sealing the fruit for one hour, and respiration by $CO_2$ production using an infrared gas analyzer (Paull and Chen, 1990). Transgenic plants are compared to the controls Cited References The following references, each of which is hereby incorporated by reference, are cited throughout the text of this application.

Ammirato, et al. 1984 Handbook of Plant Cell Culture Crop Species Macmillan Publ. Co.

An, G. 1986. Development of plant promoter expression vectors and their use of analysis of differential activity of nopaline synthetase promoter in transformed tobacco cells. Plant Physiol 81:86–91.

Arrowsmith, D. A., de Silva, J. 1995. Characterization of two tomato fruit expressed cDNA s encoding xyloglucan endo-transglycosylase. Plant Molecular Biol. 28:391–403.

Ausubel, F. M. et al., eds., 1989, Current Protocols in Molecular Biology, vol. I, Green Publishing Associates, Inc., and John Wiley & Sons, Inc., NY.

Banik, M., Garrett, T. P. J., Fincher G. B. 1996. Molecular cloning of cDNAs encoding (1 4)-beta-xylan endohydrolases from the aleurone layer of germination barley (Hordeum vulgare). Plant Molecular Biol. 31:1163–1172.

Beran, et al. 1984 Nucl. Acids Res 12:8711–8721.

Berger, et al. 1987 Guide to Molecular Cloning Techniques Academic Press, New York.

Biely, P., Mislovicová, D., Toman, R. 1985 Soluble chromogenic substrates for the assay of endo-1,4-d-xylanases and endo-1,4-d-glucanases. Analytical Biochemistry 144:142–146.

Brummell, D. A., Lashbrook, C. C., Bennett, A. B. 1994. Plant endo-1,4-beta-D-glucanase: structure, properties, and physiological function. p100–129 In. M. A. Himmel, J. O. Baker, R. P. Owen, (eds.) Enzymatic conversion of biomass for fuel production. ACS Symposium Series 566. American Chemical Soc. Washington, D.C.

Cabera-Ponce, J. L., Vega-Garcia, A., Herrera-Estrella, L. 1995. Herbicide resistant transgenic papaya plants produced by an efficient particle bombardment transformation method. Plant Cell Reports 15:1–7.

Carpita, N., Gibeaut, D. M. 1993. Structural models of primary cell walls in flowering plants: consistency of molecular structure with physical properties of the walls during growth. The Plant J. 3:1–30.

Christon 1994 Agro Food Industry Hi Tech, March/April 1994 p.17.

Christon, et al. 1991 Bio/Technology 9:957–962.

Dellaporta, S., Wood J., Hicks, J. 1983. A plant DNA minipreparation Version II. Plant Molec. Biol. Rpt. 1:19–21.

Doux-Gayat, A., Auriol, P., Josebau, J. P., Jouze, A. 1978. Degradation of muskmelon cell wall by the xylanases of Colletotrichum legeharium. Physiol. Plant 42:301–306.

Estrella, et al. 1983 Nature 303:209.

Erlich, H. A. 1989 PCR Technology Stockton Press, London.

Fischer, R. L., Bennett, A. B. 1991. Role of cell wall hydrolases in fruit ripening. Ann Rev Plant Physiol Plant Molec Biol 42: 675–703.

Risk, et al. 1993 Scientia Horticulturae 55:5–36. Fitch, M. M. M., Pang, S-Z., Slightom, J. L., Luis, S., Tennant, P., Manshardt, R. M., Gonsalves, D. 1994. II.4 Genetic transformation in Carica papaya L. (Papaya) p.236–256. In. Y. R. S. Bajay (Ed.). Biotechnology in Agriculture and Forestry, Vol 29. Plant Protoplasts and Genetic Engineering V. Springer-Verlag, Berlin, Heidelberg.

Fitch, M. M. M., Manshardt, R. M., Gonsalves, D., Slightom, J. L. 1993. Transgenic papaya plants from Agrobacterium-medicated transformation of somatic embryos. Plant Cell Reports 12:245–249.

Fromm, et al. 1990 Bio/Technology 8:833–839.

Gasser, et al. 1989 Science 244:1293.

Giovannoni, J. J., DellaPenna, D., Bennett, A. B. Fisher, R., L. 1989. Expression of a chimeric polygalacturonase gene in transgenic rin (ripening inhibitor) tomato fruit results in polyuronide degradation but not fruit softening. Plant Cell 1:53–63.

Gordon-Kamm, et al. 1990 Plant Cell 603–618.

Gross K, C. 1982 A rapid and sensitive spectrophotometric method for assaying polygalactur onase using 2-cyanoacetamide. HortScience 17:933–934.

Hepburn, A. P., White J., Pearson, L., Maunders, M. J., Clarike, L. E., Prescott, A. G., Blundy, K. S. 1985. The use of pMJ5000 as an intermediate vector for the genetic manipulation of Agrobacterium Ti plasmids. J. Gen. Microbiol. 131:2961–2969.

Innis , M. A. 1990 *PCR Protocols: A Guide to Methods and Applications* Academic Press, Inc. New York.

Kalaitzis, P., Solomos, T., Tucker, M. L. 1997. Three different polygalacturonase are expressed in tomato leaf and flower abscission, each with a different temporal expression pattern. Plant Physiol 113:1303–1308.

Jefferson, R. A. 1987. Assaying chimeric genes in plants, the GUS reporter gene fusion system. Plant Mol. Biol. Rpt 5:387–405.

Jenkins, E. S., Paul, W., Coupe, S. A. Bell, S. J., Davies, E. C., Roberts, J. A. 1996. Characterization of an mRNA encoding a polygalacturonase expressed during pod development of oilseed rape (Brassica napus L.) J Exper Bot 47:111–115.

Jenkins, E. S., Paul, W., Craze, M., Whitelaw, C. A., Weigand, A., Roberts, J. A. 1998. Dehiscence-related expression of an *Arabidopsis thaliana* gene encoding a polygalacturonase in transgenic plants of Brassica napus. Plant, Cell and Environment 22:159–167.

Klee, H. J., et al. 1984 Bio/Technology 3:637–642.

Labavitch, J. M., Greve, L. C. 1983. Cell wall metabolism in ripening fruit III. Purification of an endo-beta-1,4-xylanase that degrades a structural polysaccharide of pear fruit cell walls. Plant Physiol 72:668–673.

Lashbrook, C. C., Brummell, D. A., Rose, J. K. C., Bennett, A. B. 1994. Two divergent endo-beta-1,4-glucanase genes exhibit overlapping expression in ripening fruit and abscising flowers. The Plant Cell 6:1485–1493.

Lashbrook, C. C., Brummell, D. A., Rose, J. K. C., Bennett, A. B. 1998. Non-pectolytic cell wall metabolism during fruit ripening. In. J. J. Giovannoni (ed.). Fruit Molecular Biology. Harvard Academic, Reading , U.K. (In press-Preprt in provided by senior author).

Lashbrook., C. C., Giovannoni, J. J., Hall, B. D., Fischer, R. L., Bennett, A. B. 1998. Transgenic analysis of tomato endo-beta-1,4-glucanase gene function. Role of cel-1 in floral abscission. The Plant J. 13:303–310.

Lazo, G. R., Stein, P. A., Ludwig, R. A. 1991. A DNA transformation-component Arabidopsis genomic library in Agrobacterium. Bio/Technology 9:963–967.

Lopez-Gomez, R., Gomez-Lim, M. A. 1992. A method for extracting intact RNA from fruits rich in polysaccharides using ripe mango mesocarp. Hort Science 27:440–442.

Lienart, Y., Comtat, J., Barnoud, F. 1985. Purification of cell wall-D-xylanase from Acacia cultured cells. Plant Sci. 41:91–96.

Little, P. F. R., Jackson, I. L. 1987. Application of plasmid containing promoters specific for phage-encoded RNA polymerase. p1–18. In. D. M. Glover (ed). DNA cloning, a practical approach. IRL Press, Oxford.

Mahon, R. E., Bateson, M. F., Chamberlain, D. A., Higgins, C. M., Drew, R. A., Dale, J. L. 1996. Transformation of an australian variety of *Carica papaya* using microprojectile bombardment. Aust. J. Plant Physiol. 23:679–685.

MacKenzie, C. R., Williams, R. E. 1984 Detection of cellulase and xylanase activity in isoelectric-focused gels using agar substrate gels supported on plastic film. Can. J. Microbiol. 30:1522–1525.

McClure, B. A., Guilfoyle, T. J. 1989. Tissue print hybridization. A simple technique for detecting organ and tissue specific gene expression. Plant Molecul. Biol. 12:517–524.

McDonnell, R. E., Clark, R. D., Smith, W. A., Hinchee, M. A. 1987. A simplified method for the detection of neomycin phosphoransferase II activity in transformed plant tissue. Plant Molecul. Biol. Rep. 5:380–386.

MacLachlan, G., Brady, C. 1994. Endo-1,4-β glucanase, xyloglucanase and xyloglucan endo-transglycosylase activities versus potential substrates in ripening tomatoes. Plant Physiol. 105:965–974.

McManus, M. T., Thompson, D. S., Merriman, C., Lyne, L., Osborne, D. J. 1998. Transdifferentiation of mature cortical tissue cells to functional abscission cells in bean. Plant Physiol. 116:891–899.

Meakin, P. J., Robert, J. A. 1990. Dehiscencwe of fruit in oilseed rape (Brassica napus L.). J Exper Bot 41:1003–1011.

Miller, A. R., Dalmasso, J. P., Kretchman, D. W. 1987. Mechanical stress, storage time, and temperature influence cell wall degrading enzymes, firmness and ethylene production by cucumber. J. Amer. Soc. Hort. Sci. 112:666–671.

Miller A. R., Dalmasso, J. P., Kretchman, D. W. 1989. Developmental variation of cell wall degrading enzymes from cucumber (*Cucumis sativus*) fruit tissue. Can. J. Bot. 67:817–821.

O'Brien 1990 *Genetic Maps: Cocus Maps of Complex Genomes, Book 5 Human Maps* Cold Spring Harbor Laboratory Press.

Osborne, D. J. 1989. Abscission. CRC Critical Rev Plant Sci. 2:103–129

Paull, R. E., Chen, N. J. 1983. Postharvest variation in cell wall degrading enzymes of papaya during fruit ripening. Plant Physiol. 72:382–385.

Paull, R. E., Gross, K., Qiu, Y. X. 1998. Changes in papaya cell walls during fruit ripening. Postharvest Biol. Technol. 16:79–89.

Perl, A., Kles, H., Galil, G., Galun, E. 1992. Improvement of plant regeneration and GUS expression in scutella wheat calli by optimization of culture conditions and DNA-microprojectile delivery conditions. Molec. General Genetics 235:279–284.

Petersen, M., Sanders, I., Child, R., Onckelen, H., van, Ulvskar, P., Borkhardt, B. 1996. Isolation and characterization of a pod dehiscence zone-specific polygalacturonase from Brassica napus. Plant Molecular Biol. 31:517–527.

Reid, P. D., Pont-Lezica, R. F. (Editors) 1992. Tissue Printing: Tools for the study of anatomy, histochemistry, and gene expression. Academic Press, San Diego, Calif.

Ronen, R., Zauberman, G., Akerman, M., Weksler, A., Rot, I., Fucks, Y. 1991. Xylanase and xylosidase activities in avocado fruit. Plant Physiol. 95:961–964.

Rose, J. K. C., Hadfield, K. A., Labavitch, J. M., Bennett, A. B. 1998. Temporal sequence of cell wall disassembly in rapidly ripening melon fruit. Plant Physiol. 117:345–361.

Sambrook, J., Fritsch, E. F., Maniatis, T. 1989. Molecular Cloning. A laboratory Manual. $2^{nd}$ Edition. Cold Spring Harbor, N.Y.

Sexton, R. 1995. Abscission. P497–525. In. M. Pessarakli, ed. Handbook of plant and crop physiology. Marcel Dekker, N.Y.

Shimamoto, et al. 1989 Nature 338:274–276.

Slade, A. M., Hoy, P. B., Morrice, N. A., Fincher, G. B. 1989. The purification and characterization of three (1-4)-beta-xylan endohydrolyases from germinated barley. Eur. J. Biochem. 185:533–539.

Smith, C. J. S., Watson, C. F. S., Ray, J., Bird, C. R., Morris, P. C., Schuch, W., Grierson, D. 1988. Antisense RNA inhibition of polygalacturonase gene expression in transgenic tomatoes. Nature 334:724–726.

Smith, D. L., Starrett, D. A., Gross, K. C. 1998. A gene encoding for tomato fruit—galactosidase II is expressed during fruit ripening. Plant Physiol. 117:417–423.

Spruce, J., Mayer, A. M., Osborne, D. J. 1987. A simple histochemical method for localizing enzyme in plant tissue using nitrocellulose blotting. Phytochemistry 26:2901–2903.

Sunna, A., Anthranikian, G. 1997. Xylanolytic enzymes from fungi and bacteria. Critical Rev. Biotechnology 17:39–67.

Taiz, L. 1984. Plant cell expansion; regulation of cell wall mechanical properties. Ann. Rev. Plant Physiol 35:585–657.

Tieman, D. M., Harriman, R. W., Ramamohan, G., Handa, A. K. 1992. An antisense pectin methylesterase alters pectin chemistry and soluble solids in tomato fruit. Plant Cell 4:667–679.

Tieman, D. M., Handa, A. K. 1989. Immunocytolocalization of polygalacturonase in ripening tomato fruits. Plant Physiol. 90:17–20.

Uze, M., et al., 1997 Plant Science 130:87.

Vasil, et al. 1990 Bio/Technology 8:429–434.

Wong, K. K. Y., Tan, L. U. L., Saddler, J. N. 1988. Multiplicity of a -1,4-xylanase in micro organisms: functions and applications. Microbiol. Rev. 52:305–317.

Yamaki, S., Kakiuchi, N. 1979. Changes in hemicellulose-degrading enzymes during development and ripening of Japanese pear fruit. Plant Cell Physiol. 20:301–309.

The invention having now been described is now illustrated by way of the following non-limited claims.

We claim:

1. An isolated and purified nucleic acid comprising the sequence of SEQ ID NO:24.

2. The nucleic acid of claim 1 operably linked to a promoter.

3. The nucleic acid of claim 2 wherein said promoter is functional in a plant cell.

4. A cell comprising at least one copy of a nucleic acid having a sequence of SEQ NO:24 wherein said cell or ancestor of said cell was transformed with a vector including said nucleic acid.

5. The cell of claim 4 wherein said nucleic acid is operably linked to a promoter functional in said cell.

6. The cell of claim 4 wherein said cell is an eukaryotic cell.

7. The cell of claim 4 wherein said cell is a prokaryotic cell.

8. The cell of claim 6 wherein said cell is a plant cell.

9. The cell of claim 8 wherein said cell is a papaya cell.

10. A plant comprising a nucleic acid introduced into said plant by transformation wherein said nucleic acid has the nucleotide sequence of SEQ ID NO: 24.

11. The plant of claim 10 wherein said nucleic acid is operably linked to a promoter.

* * * * *

SEQUENCE LISTING

```
<160> NUMBER OF SEQ ID NOS: 33

<210> SEQ ID NO 1
<211> LENGTH: 17
<212> TYPE: PRT
<213> ORGANISM: Carica papaya L.

<400> SEQUENCE: 1

Lys Asn Gly Ile Ala Ile Arg Gly His Asn Val Phe Trp Asp Asp Pro
1               5                   10                  15

Lys

<210> SEQ ID NO 2
<211> LENGTH: 31
<212> TYPE: PRT
<213> ORGANISM: Carica papaya L.

<400> SEQUENCE: 2

Arg Ile Asn Ser Val Met Asn Arg Tyr Lys Gly Gln Val Ile Gly Trp
1               5                   10                  15

Asp Val Val Asn Glu Asn Leu His Phe Ser Phe Phe Glu Ser Lys
            20                  25                  30

<210> SEQ ID NO 3
<211> LENGTH: 27
<212> TYPE: PRT
<213> ORGANISM: Carica papaya L.

<400> SEQUENCE: 3

Thr Asp Pro Ser Thr Thr Leu Phe Met Asn Glu Tyr Asn Thr Val Glu
1               5                   10                  15

Asp Ser Arg Asp Gly Gln Ala Thr Pro Ala Lys
            20                  25

<210> SEQ ID NO 4
<211> LENGTH: 22
<212> TYPE: PRT
<213> ORGANISM: Carica papaya L.

<400> SEQUENCE: 4

Leu Arg Ser Ile Gln Ser Leu Pro Gly Asn Gly Asn Met Gly Ile Gly
1               5                   10                  15

Leu Glu Ser His Phe Ser
            20
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Degenerate
      primer based upon the amino acid sequence of
      purified papaya xylanase.
<221> NAME/KEY: misc_feature
<222> LOCATION: (1)...(20)
<223> OTHER INFORMATION: n = A, T, C, or G

<400> SEQUENCE: 5
cawgtnathg gntgggaygt                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Degenerate
      primer based upon the amino acid sequence of
      purified papaya xylanase.
<221> NAME/KEY: misc_feature
<222> LOCATION: (1)...(20)
<223> OTHER INFORMATION: n = A, T, C, or G

<400> SEQUENCE: 6
tgggaygtng tnaaygawaa                                                    20

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Degenerate
      primer based upon the amino acid sequence of
      purified papaya xylanase.
<221> NAME/KEY: misc_feature
<222> LOCATION: (1)...(23)
<223> OTHER INFORMATION: n = A, T, C, or G

<400> SEQUENCE: 7
cayaaygtnt tytgggayga ycc                                                23

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Degenerate
      primer based upon the amino acid sequence of
      purified papaya xylanase.
<221> NAME/KEY: misc_feature
<222> LOCATION: (1)...(20)
<223> OTHER INFORMATION: n = A, C, T, or G

<400> SEQUENCE: 8
acwtcccanc cdatnacytg                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Degenerate
      primer based upon the amino acid sequence of
      purified papaya xylanase.
<221> NAME/KEY: misc_feature

```
<222> LOCATION: (1)...(20)
<223> OTHER INFORMATION: n = A, T, C, or G

<400> SEQUENCE: 9
ttytcwttna cnacwtccca                                              20

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Degenerate
      primer based upon the amino acid sequence of
      purified papaya xylanase.
<221> NAME/KEY: misc_feature
<222> LOCATION: (1)...(23)
<223> OTHER INFORMATION: n = A, T, C, or G

<400> SEQUENCE: 10
ggwtcwtccc awaanacwtt wtg                                          23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Degenerate
      primer based upon the amino acid sequence of
      purified papaya xylanase.
<221> NAME/KEY: misc_feature
<222> LOCATION: (1)...(23)
<223> OTHER INFORMATION: n = A, C, T, or G

<400> SEQUENCE: 11
ttyatgaayg awtayaayac ngt                                          23

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Degenerate
      primer based upon the amino acid sequence of
      purified papaya xylanase.
<221> NAME/KEY: misc_feature
<222> LOCATION: (1)...(20)
<223> OTHER INFORMATION: n = A, C, T, or G

<400> SEQUENCE: 12
aayggnaaya tgggnathgg                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Degenerate
      primer based upon the amino acid sequence of
      purified papaya xylanase.
<221> NAME/KEY: misc_feature
<222> LOCATION: (1)...(20)
<223> OTHER INFORMATION: n = A, C, T, or G

<400> SEQUENCE: 13
ccdatnccca twttnccwtt                                              20

<210> SEQ ID NO 14
<211> LENGTH: 23
<212> TYPE: DNA
```

```
<213> ORGANISM: Artificial Sequence
<220> FEATURE:
<223> OTHER INFORMATION: Description of Artificial Sequence: Degenerate
      primer based upon the amino acid sequence of
      purified papaya xylanase.
<221> NAME/KEY: misc_feature
<222> LOCATION: (1)...(23)
<223> OTHER INFORMATION: n = A, T, C, or G

<400> SEQUENCE: 14
acngtwttwt aytcwttcat waa                                            23

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Degenerate
      primer based upon the amino acid sequence of
      purified papaya xylanase.
<221> NAME/KEY: misc_feature
<222> LOCATION: (1)...(18)
<223> OTHER INFORMATION: n = A, T, C, or G

<400> SEQUENCE: 15
ggncayaayg tttytggg                                                  18

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Degenerate
      primer based upon the amino acid sequence of
      purified papaya xylanase.
<221> NAME/KEY: misc_feature
<222> LOCATION: (1)...(19)
<223> OTHER INFORMATION: n = A, T, C, or G

<400> SEQUENCE: 16
ggnatgaaym gtataawgg                                                 19

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Degenerate
      primer based upon the amino acid sequence of
      purified papaya xylanase.
<221> NAME/KEY: misc_feature
<222> LOCATION: (1)...(21)
<223> OTHER INFORMATION: n = A, T, C, or G

<400> SEQUENCE: 17
ccdatcccat wttccwttnc c                                              21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Papaya
      xylanase gene specific primer.

<400> SEQUENCE: 18
tggcgaagct cataagactg                                                20

<210> SEQ ID NO 19
```

```
<211> LENGTH: 20
<212> TYPE: DNA
<213> ORGANISM: Artificial Sequence
<220> FEATURE:
<223> OTHER INFORMATION: Description of Artificial Sequence: Papaya
      xylanase gene specific primer.

<400> SEQUENCE: 19
gttgttgatg gatcagtctt                                                  20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Papaya
      xylanase gene specific primer.

<400> SEQUENCE: 20
cgaagtatca atcaggatgg                                                  20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Papaya
      xylanase gene specific primer.

<400> SEQUENCE: 21
ggttggtaag ttgtggaagt                                                  20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Papaya
      xylanase gene specific primer.

<400> SEQUENCE: 22
atggaagagt gagctctgaa                                                  20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Papaya
      xylanase gene specific primer.

<400> SEQUENCE: 23
ccaaccaata acttgacctt                                                  20

<210> SEQ ID NO 24
<211> LENGTH: 1752
<212> TYPE: DNA
<213> ORGANISM: Carica papaya L.

<400> SEQUENCE: 24
atgaagcttg gagagaagaa cttacagttt tattttctgc tggtgctgcc gtacgccctc      60 cttttccag gactggagac caatgctcta tcctacgatt acacagctag tattcagtgt     120
ttggagaatc ctcaaaaagc acaatatgga ggaggaatca tcacaaaccc agagttgaat     180
caagggttga aaggctggtc aacttttgga gatgcaaaaa ttcaacacag agttgcagga     240
```

-continued

```
tctaacagct tcattgtggc tcataccagg tctcaacccc atgatagtgt ctcccagacc      300
ctgtacttgc aaagcaacaa gctctacact ttctctgcct ggatacgagt aagtgaagga      360
aagactcctg taaaggctat tttcaaaaca agtctgggt acaaatatgc tggtgctgtt       420
gtggctgagt ccaattgttg gtccatgctt aaaggtggtc tcactgttga tgcatcaggt     480
cctgcagaac tttactttga gactgataac acatcagttg agatttggat tgatagcatt    540
tcactccaac cattcactca acaagaatgg aaatctcatc aggatcaaag cattaagaag     600
attagaaaga agaatgtgag aattcaagca gttgacaagc ttgggaatcc tttacccaac     660
acaacggtct caatatcacc aaagaaaatt ggtttcccat ttgggtgtgc tataaataga     720
aacattgtga ataacaatgc atatcaaagt tggttttcat ctagatttac agtgacaaca     780
ttcgagaacg aaatgaagtg ggcgagcacc gaaccaagtc aaggccacga ggactactca     840
acagccgatg ccatggttca attcgctaag aaaaatggca tagcaatccg tggacacaac     900
gtgttttggg atgatccgaa gtatcaatca ggatgggtga gttcactctc acccaatgat     960
cttaatgctg ctgcaacaaa aagaataaat tctgtgatga acagatataa aggtcaagtt    1020
attggttggg atgtggttaa tgaaaattta cacttttctt tcttcgaaag caagcttggt    1080
gcaaatgctt ccgctgtgtt ttatggcgaa gctcataaga ctgatccatc aacaacattg    1140
tttatgaatg aatataatac tgtggaggat agtagagatg acaagcaac accggctaag     1200
tatctcgaaa agctgaggtc gatccaatca ttgcctggta atggtaacat ggggattggt    1260
ctcgagtctc atttcagtag tagtcctcca aatattccat acatgagatc agccatcgac    1320
actctcgctg ccactggatt acctgtttgg cttacagaag tcgacgttca aagtggtgga    1380
aaccaagcgc aaagcttaga acagattcta agagaggcac attcgcatcc gaaagtgaga    1440
gggattgtaa tatggtcagc gtggtcacca aacggatgtt atcgtatgtg tttaaccgac    1500
aataacttcc acaacttacc aaccggagat gttgtcgata agcttttgcg cgaatggggc    1560
ggcggcgcca ccgttaaggg caaaactgat cagaatggtt tctttcagag ctcactcttc    1620
catggagatt atgagatcaa agtccaggtc aaccacccat caagttacc ttcttcctca    1680
tctcatcata ccttcaaatt gaattcaaca gatgatgaat ccaaacaaac aagattactt    1740
ctcattaaag tt                                                          1752
```

<210> SEQ ID NO 25
<211> LENGTH: 584
<212> TYPE: PRT
<213> ORGANISM: Carica papaya L.

<400> SEQUENCE: 25

```
Met Lys Leu Gly Glu Lys Asn Leu Gln Phe Tyr Phe Leu Leu Val Leu
  1               5                  10                  15

Pro Tyr Ala Leu Leu Phe Pro Gly Leu Glu Thr Asn Ala Leu Ser Tyr
             20                  25                  30

Asp Tyr Thr Ala Ser Ile Gln Cys Leu Glu Asn Pro Gln Lys Ala Gln
         35                  40                  45

Tyr Gly Gly Gly Ile Ile Thr Asn Pro Glu Leu Asn Gln Gly Leu Lys
     50                  55                  60

Gly Trp Ser Thr Phe Gly Asp Ala Lys Ile Gln His Arg Val Ala Gly
 65                  70                  75                  80

Ser Asn Ser Phe Ile Val Ala His Thr Arg Ser Gln Pro His Asp Ser
                 85                  90                  95

Val Ser Gln Thr Leu Tyr Leu Gln Ser Asn Lys Leu Tyr Thr Phe Ser
```

-continued

```
                100                 105                 110
Ala Trp Ile Arg Val Ser Glu Gly Lys Thr Pro Val Lys Ala Ile Phe
            115                 120                 125
Lys Thr Lys Ser Gly Tyr Lys Tyr Ala Gly Ala Val Ala Glu Ser
130                 135                 140
Asn Cys Trp Ser Met Leu Lys Gly Gly Leu Thr Val Asp Ala Ser Gly
145                 150                 155                 160
Pro Ala Glu Leu Tyr Phe Glu Thr Asp Asn Thr Ser Val Glu Ile Trp
                165                 170                 175
Ile Asp Ser Ile Ser Leu Gln Pro Phe Thr Gln Gln Glu Trp Lys Ser
            180                 185                 190
His Gln Asp Gln Ser Ile Lys Lys Ile Arg Lys Asn Val Arg Ile
            195                 200                 205
Gln Ala Val Asp Lys Leu Gly Asn Pro Leu Pro Asn Thr Thr Val Ser
210                 215                 220
Ile Ser Pro Lys Lys Ile Gly Phe Pro Phe Gly Cys Ala Ile Asn Arg
225                 230                 235                 240
Asn Ile Val Asn Asn Ala Tyr Gln Ser Trp Phe Ser Ser Arg Phe
                245                 250                 255
Thr Val Thr Thr Phe Glu Asn Glu Met Lys Trp Ala Ser Thr Glu Pro
            260                 265                 270
Ser Gln Gly His Glu Asp Tyr Ser Thr Ala Asp Ala Met Val Gln Phe
            275                 280                 285
Ala Lys Lys Asn Gly Ile Ala Ile Arg Gly His Asn Val Phe Trp Asp
            290                 295                 300
Asp Pro Lys Tyr Gln Ser Gly Trp Val Ser Ser Leu Ser Pro Asn Asp
305                 310                 315                 320
Leu Asn Ala Ala Ala Thr Lys Arg Ile Asn Ser Val Met Asn Arg Tyr
                325                 330                 335
Lys Gly Gln Val Ile Gly Trp Asp Val Val Asn Glu Asn Leu His Phe
            340                 345                 350
Ser Phe Phe Glu Ser Lys Leu Gly Ala Asn Ala Ser Ala Val Phe Tyr
            355                 360                 365
Gly Glu Ala His Lys Thr Asp Pro Ser Thr Thr Leu Phe Met Asn Glu
370                 375                 380
Tyr Asn Thr Val Glu Asp Ser Arg Asp Gly Gln Ala Thr Pro Ala Lys
385                 390                 395                 400
Tyr Leu Glu Lys Leu Arg Ser Ile Gln Ser Leu Pro Gly Asn Gly Asn
                405                 410                 415
Met Gly Ile Gly Leu Glu Ser His Phe Ser Ser Pro Pro Asn Ile
            420                 425                 430
Pro Tyr Met Arg Ser Ala Ile Asp Thr Leu Ala Ala Thr Gly Leu Pro
            435                 440                 445
Val Trp Leu Thr Glu Val Asp Val Gln Ser Gly Gly Asn Gln Ala Gln
450                 455                 460
Ser Leu Glu Gln Ile Leu Arg Glu Ala His Ser His Pro Lys Val Arg
465                 470                 475                 480
Gly Ile Val Ile Trp Ser Ala Trp Ser Pro Asn Gly Cys Tyr Arg Met
                485                 490                 495
Cys Leu Thr Asp Asn Asn Phe His Asn Leu Pro Thr Gly Asp Val Val
            500                 505                 510
Asp Lys Leu Leu Arg Glu Trp Gly Gly Ala Thr Val Lys Gly Lys
            515                 520                 525
```

-continued

```
Thr Asp Gln Asn Gly Phe Phe Gln Ser Ser Leu Phe His Gly Asp Tyr
        530                 535                 540

Glu Ile Lys Val Gln Val Asn His Pro Ser Lys Leu Pro Ser Ser Ser
545                 550                 555                 560

Ser His His Thr Phe Lys Leu Asn Ser Thr Asp Asp Glu Ser Lys Gln
                565                 570                 575

Thr Arg Leu Leu Leu Ile Lys Val
            580

<210> SEQ ID NO 26
<211> LENGTH: 461
<212> TYPE: PRT
<213> ORGANISM: Streptomyces halstedii

<400> SEQUENCE: 26

Met Ala Gln Asn Pro Pro Val Gly Gly Arg Thr Arg Arg Pro Gln
  1               5                  10                  15

Ala Arg Ala Arg Cys Ala Leu Ser Leu Leu Thr Ala Gly Val Leu Ala
                 20                  25                  30

Ala Ala Gly Val Val Ala Leu Ala Gly Thr Ala Gln Ala Ala Gly Ala
             35                  40                  45

Leu Gly Asp Ala Ala Ala Lys Gly Arg Tyr Phe Gly Ala Ala Val
 50                  55                  60

Ala Ala Asn His Leu Gly Glu Ala Ala Tyr Ala Ser Thr Leu Asp Ala
 65                  70                  75                  80

Gln Phe Gly Ser Val Thr Pro Glu Asn Glu Met Lys Trp Asp Ala Val
                 85                  90                  95

Glu Ser Ser Arg Asn Ser Phe Ser Phe Ser Ala Ala Asp Arg Ile Val
                100                 105                 110

Ser His Ala Gln Ser Lys Gly Met Lys Val Arg Gly His Thr Leu Val
            115                 120                 125

Trp His Ser Gln Leu Pro Gly Trp Val Ser Pro Leu Ala Ala Thr Asp
130                 135                 140

Leu Arg Ser Ala Met Asn Asn His Ile Thr Gln Val Met Thr His Tyr
145                 150                 155                 160

Lys Gly Lys Ile His Ser Trp Asp Val Val Asn Glu Ala Phe Gln Asp
                165                 170                 175

Gly Gly Ser Gly Ala Arg Arg Ser Ser Pro Phe Gln Asp Lys Leu Gly
            180                 185                 190

Asn Gly Phe Ile Glu Glu Ala Phe Arg Thr Ala Arg Thr Val Asp Ala
        195                 200                 205

Asp Ala Lys Leu Cys Tyr Asn Asp Tyr Asn Thr Asp Gly Gln Asn Ala
210                 215                 220

Lys Ser Asn Ala Val Tyr Glu Met Val Lys Asp Phe Lys Gln Arg Gly
225                 230                 235                 240

Val Pro Ile Asp Cys Val Gly Phe Gln Ser His Phe Asn Ser Asn Ser
                245                 250                 255

Pro Val Pro Ser Asp Phe Gln Ala Asn Leu Gln Arg Phe Ala Asp Leu
            260                 265                 270

Gly Val Asp Val Gln Ile Thr Glu Leu Asp Ile Glu Gly Ser Gly Ser
        275                 280                 285

Ala Gln Ala Ala Asn Tyr Thr Lys Val Val Asn Ala Cys Leu Ala Val
    290                 295                 300

Thr Arg Cys Thr Gly Ile Thr Val Trp Gly Val Thr Asp Lys Tyr Ser
```

```
                    305                 310                 315                 320
Trp Arg Ser Gly Gly Thr Pro Leu Leu Phe Asp Gly Asp Tyr Asn Lys
                325                 330                 335

Lys Pro Ala Tyr Asp Ala Val Leu Ala Ala Leu Gly Gly Ser Gly Gly
                340                 345                 350

Gly Gly Asp Asp Gly Gly Glu Gly Asp Gly Ala Cys Thr Ala Thr
                355                 360                 365

Tyr Thr Arg Thr Ser Thr Trp Asn Gly Gly Tyr Asn Gly Gln Val Thr
                370                 375                 380

Val Lys Ala Gly Gly Ser Gly Ile Thr Gly Trp Ala Val Pro Val Thr
385                 390                 395                 400

Val Ala Ser Pro Gln Lys Val Ser Ala Val Trp Asn Gly Thr Pro Thr
                405                 410                 415

Thr Thr Gly Asp Val Met Thr Val Arg His Ser Trp Asn Gly Thr Leu
                420                 425                 430

Ala Ala Gly Ala Ser Thr Thr Phe Gly Phe Thr Val Gln Thr Asn Gly
                435                 440                 445

Gly Thr Ser Ala Pro Val Val Gly Ala Cys Thr Ala Ser
                450                 455                 460

<210> SEQ ID NO 27
<211> LENGTH: 327
<212> TYPE: PRT
<213> ORGANISM: Aspergillus oryzae

<400> SEQUENCE: 27

Met Val His Leu Lys Ala Leu Ala Ser Gly Thr Leu Phe Ala Ser Leu
1               5                   10                  15

Ala Ser Ser Ala Val Ile Ser Arg Gln Ala Ala Ala Ser Ile Asn Asp
                20                  25                  30

Ala Phe Val Ala His Gly Lys Lys Tyr Phe Gly Thr Cys Ser Asp Gln
                35                  40                  45

Ala Leu Leu Gln Asn Ser Gln Asn Glu Ala Ile Val Arg Ala Asp Phe
    50                  55                  60

Gly Gln Leu Thr Pro Glu Asn Ser Met Lys Trp Asp Ala Leu Glu Pro
65                  70                  75                  80

Ser Gln Gly Ser Phe Ser Phe Ala Gly Ala Asp Phe Leu Ala Asp Tyr
                85                  90                  95

Ala Lys Thr Asn Asn Lys Leu Val Arg Gly His Thr Leu Val Trp His
                100                 105                 110

Ser Gln Leu Pro Ser Trp Val Gln Gly Ile Thr Asp Lys Asp Thr Leu
                115                 120                 125

Thr Glu Val Ile Lys Asn His Ile Thr Thr Ile Met Gln Arg Tyr Lys
    130                 135                 140

Gly Gln Ile Tyr Ala Trp Asp Val Val Asn Glu Ile Phe Asp Glu Asp
145                 150                 155                 160

Gly Thr Leu Arg Asp Ser Val Phe Ser Gln Val Leu Gly Glu Asp Phe
                165                 170                 175

Val Arg Ile Ala Phe Glu Thr Ala Arg Glu Ala Asp Pro Asn Ala Lys
                180                 185                 190

Leu Tyr Ile Asn Asp Tyr Asn Leu Asp Ser Ala Asp Tyr Ala Lys Thr
                195                 200                 205

Lys Gly Met Val Ser Tyr Val Lys Lys Trp Leu Asp Ala Gly Val Pro
    210                 215                 220
```

```
Ile Asp Gly Ile Gly Ser Gln Ser His Tyr Ser Ala Asn Gly Phe Pro
225                 230                 235                 240

Val Ser Gly Ala Lys Gly Ala Leu Thr Ala Leu Ala Ser Thr Gly Val
            245                 250                 255

Ser Glu Val Ala Val Thr Glu Leu Asp Ile Glu Gly Ala Ser Ser Glu
            260                 265                 270

Ser Tyr Leu Glu Val Val Asn Ala Cys Leu Asp Val Ser Ser Cys Val
            275                 280                 285

Gly Ile Thr Val Trp Gly Val Ser Asp Lys Asp Ser Trp Arg Ser Ser
290                 295                 300

Thr Ser Pro Leu Leu Phe Asp Ser Asn Tyr Gln Ala Lys Asp Ala Tyr
305                 310                 315                 320

Asn Ala Ile Ile Asp Ala Leu
                325

<210> SEQ ID NO 28
<211> LENGTH: 427
<212> TYPE: PRT
<213> ORGANISM: Hordeum vulgare

<400> SEQUENCE: 28

Met Gly Ala Phe Arg Leu Arg Thr Glu Pro Arg Ser Ala Ala Val Tyr
1               5                   10                  15

Val His Gly Ala Pro Ala Gly Val Asp Val Lys Val Met Asp Leu Arg
            20                  25                  30

Val Tyr Pro Val Asp His Lys Ala Arg Phe Arg Gln Leu Lys Asp Lys
            35                  40                  45

Thr Asp Lys Ala Arg Lys Arg Asp Val Ile Leu Lys Leu Gly Thr Pro
50                  55                  60

Ala Gly Ala Gly Ala Ala Ala Ser Val Arg Val Val Gln Leu
65                  70                  75                  80

Asp Asn Ala Phe Pro Phe Gly Thr Cys Ile Asn Thr Ser Val Ile Gln
                85                  90                  95

Lys Pro Ala Phe Leu Asp Phe Phe Thr Asn His Phe Asp Trp Ala Val
            100                 105                 110

Phe Glu Asn Glu Leu Lys Trp Tyr His Thr Glu Val Gln Gln Gly Gln
            115                 120                 125

Leu Asn Tyr Ala Asp Ala Asp Ala Leu Leu Ala Phe Cys Asp Arg Leu
130                 135                 140

Gly Lys Thr Val Arg Gly His Cys Val Phe Trp Ser Val Asp Gly Asp
145                 150                 155                 160

Val Gln Gln Trp Val Lys Asn Leu Asn Lys Asp Gln Leu Arg Ser Ser
                165                 170                 175

Met Gln Ser Arg Leu Glu Gly Leu Val Ser Arg Tyr Ala Gly Arg Phe
            180                 185                 190

Lys His Tyr Asp Val Asn Asn Glu Met Leu His Gly Arg Phe Phe Arg
            195                 200                 205

Asp Arg Leu Gly Asp Glu Asp Val Pro Ala Tyr Met Phe Lys Glu Val
210                 215                 220

Ala Arg Leu Asp Pro Glu Pro Val Leu Phe Val Asn Asp Tyr Asn Val
225                 230                 235                 240

Glu Cys Gly Asn Asp Pro Asn Ala Thr Pro Glu Lys Tyr Ala Glu Gln
                245                 250                 255

Val Ala Trp Leu Gln Ser Cys Gly Ala Val Val Arg Gly Ile Gly Leu
            260                 265                 270
```

-continued

```
Gln Gly His Val Gln Asn Pro Val Gly Glu Val Ile Cys Ala Ala Leu
            275                 280                 285

Asp Arg Leu Ala Lys Thr Gly Val Pro Thr Trp Phe Thr Glu Leu Asp
    290                 295                 300

Val Pro Glu Tyr Asp Val Gly Leu Arg Ala Lys Asp Leu Glu Val Val
305                 310                 315                 320

Leu Arg Glu Ala Tyr Ala His Pro Ala Val Glu Gly Ile Val Phe Trp
                325                 330                 335

Gly Phe Met Gln Gly Thr Met Trp Arg Gln Asn Ala Trp Leu Val Asp
            340                 345                 350

Ala Asp Gly Thr Val Asn Glu Ala Gly Gln Met Phe Leu Asn Leu Gln
        355                 360                 365

Lys Glu Trp Lys Thr Asp Ala Arg Gly Asn Phe Asp Gly Asp Gly Asn
    370                 375                 380

Phe Lys Phe Arg Gly Phe Tyr Gly Arg Tyr Val Val Glu Val Thr Thr
385                 390                 395                 400

Ala Lys Arg Lys Gln Met Leu Lys Thr Phe Thr Val Glu Lys Gly Asp
                405                 410                 415

Asn Thr Pro Val Val Asp Leu Ala Asp Ala
            420                 425

<210> SEQ ID NO 29
<211> LENGTH: 1063
<212> TYPE: PRT
<213> ORGANISM: Arabidopsis thaliana

<400> SEQUENCE: 29

Met Ala Asp Leu Asn Ile Val Met Asn Gly Asp Phe Phe Ala Gly Ile
1               5                   10                  15

Glu Pro Trp Tyr Pro Asn Gly Cys Glu Ala Phe Val Val Ser Ser Asp
            20                  25                  30

Pro Phe Ser Ser Glu Val Met Ser Ala Asp Ser Ser Gly Gly Tyr
        35                  40                  45

Val Val Val Thr Asn Arg Lys Glu Thr Trp Gln Gly Leu Glu Gln Asp
    50                  55                  60

Ile Thr Thr Arg Val Ala Ser Gly Met Asn Tyr Thr Val Ser Thr Cys
65                  70                  75                  80

Val Gly Val Ser Gly Pro Phe Asn Glu Ser Ala Glu Val Leu Ser Thr
                85                  90                  95

Val Arg Leu Glu His Glu Asp Ser Pro Thr Glu Tyr Leu Cys Ile Gly
            100                 105                 110

Lys Thr Tyr Ala Ser Arg Asp Lys Trp Val Asp Leu Glu Gly Thr Phe
        115                 120                 125

Ser Ile Ser Asn Met Pro Asp Arg Val Val Leu Tyr Leu Glu Gly Pro
    130                 135                 140

Ala Pro Gly Lys Asp Leu Leu Ile Arg Ser Val Thr Arg Ser Ser
145                 150                 155                 160

Thr Ser Ser Asp Phe Gln Glu Thr Glu Lys Asn Thr Asp Ala Ser Asn
                165                 170                 175

Val Phe Pro Leu Ala Leu Asn Ile Ile Lys Asn His Asp Phe Ser Asp
            180                 185                 190

Gly Leu Tyr Ser Trp Asn Thr Asn Gly Cys Asp Ser Phe Val Val Ser
        195                 200                 205

Ser Asn Asp Cys Asn Leu Glu Ser Asn Ala Val Val Asn Asn Arg Ser
```

-continued

```
            210                 215                 220
Glu Thr Trp Gln Gly Leu Glu Gln Asp Ile Thr Asp Asn Val Ser Pro
225                 230                 235                 240

Gly Phe Ser Tyr Lys Val Ser Ala Ser Val Ser Val Ser Gly Pro Val
                245                 250                 255

Leu Gly Ser Ala Gln Val Leu Ala Thr Leu Lys Leu Glu His Lys Ser
                260                 265                 270

Ser Ala Thr Glu Phe Gln Leu Ile Gly Lys Thr Tyr Ala Ser Lys Asp
            275                 280                 285

Ile Trp Lys Thr Leu Glu Gly Thr Phe Glu Val Ser Gly Arg Pro Asp
290                 295                 300

Arg Val Val Phe Phe Leu Glu Gly Pro Pro Gly Ile Asp Leu Leu
305                 310                 315                 320

Val Lys Ser Val Thr Ile His Cys Glu Ser Asp Asn Gln Phe Glu Arg
                325                 330                 335

Ser Arg Glu Phe Cys Ser Ala Pro Glu Ser Asp Asn His Ile Phe Leu
                340                 345                 350

Asn Ser Ser Phe Ser Asp Gly Leu Asn His Trp Ser Gly Arg Gly Cys
            355                 360                 365

Asn Leu Met Leu His Glu Ser Leu Ala Asp Gly Lys Ile Leu Pro Asp
370                 375                 380

Ser Gly Thr Cys Phe Ala Ser Ala Ser Glu Arg Thr His Lys Trp Ser
385                 390                 395                 400

Gly Ile Glu Gln Asp Ile Thr Glu Arg Val Gln Arg Lys Leu Ile Tyr
                405                 410                 415

Glu Ala Ser Ser Val Val Arg Leu Ser His Ser His Thr Val Gln
                420                 425                 430

Ala Thr Leu Tyr Val Gln Tyr Leu Asp Gln Arg Glu Glu Tyr Ile Gly
            435                 440                 445

Ile Ser Ser Val Gln Gly Thr His Asp Asp Trp Val Glu Leu Lys Gly
            450                 455                 460

Lys Phe Leu Leu Asn Gly Ser Pro Ala Arg Ala Val Val Tyr Ile Glu
465                 470                 475                 480

Gly Pro Pro Gly Ile Asp Val Phe Val Asp His Phe Ala Val Lys
                485                 490                 495

Pro Ala Glu Lys Glu Thr Pro Ser Gly Arg Pro Tyr Ile Glu Ser His
                500                 505                 510

Ala Phe Gly Met Asn Ile Val Ser Asn Ser His Leu Ser Asp Gly Thr
            515                 520                 525

Ile Glu Gly Trp Phe Pro Leu Gly Asp Cys His Leu Lys Val Gly Asp
            530                 535                 540

Gly Ser Pro Arg Ile Leu Pro Pro Leu Ala Arg Asp Ser Leu Arg Lys
545                 550                 555                 560

Thr Gln Gly Tyr Leu Ser Gly Arg Tyr Val Leu Ala Thr Asn Arg Ser
                565                 570                 575

Gly Thr Trp Met Gly Pro Ala Gln Thr Ile Thr Asp Lys Val Lys Leu
                580                 585                 590

Phe Val Thr Tyr Gln Val Ser Ala Trp Val Lys Ile Gly Ser Gly Gly
            595                 600                 605

Arg Thr Ser Pro Gln Asp Val Asn Ile Ala Leu Ser Val Asp Gly Asn
            610                 615                 620

Trp Val Asn Gly Gly Lys Val Glu Val Asp Asp Gly Asp Trp His Glu
625                 630                 635                 640
```

-continued

Val Val Gly Ser Phe Arg Ile Glu Lys Glu Ala Lys Glu Val Met Leu
                645                 650                 655

His Val Gln Gly Pro Ser Pro Gly Val Asp Leu Met Val Ala Gly Leu
            660                 665                 670

Gln Ile Phe Ala Val Asp Arg Lys Ala Arg Leu Ser Tyr Leu Arg Gly
        675                 680                 685

Gln Ala Asp Val Val Arg Lys Arg Asn Val Cys Leu Lys Phe Ser Gly
    690                 695                 700

Leu Asp Pro Ser Glu Leu Ser Gly Ala Thr Val Lys Ile Arg Gln Thr
705                 710                 715                 720

Arg Asn Ser Phe Pro Leu Gly Ser Cys Ile Ser Arg Ser Asn Ile Asp
                725                 730                 735

Asn Glu Asp Phe Val Asp Phe Phe Leu Asn Asn Phe Asp Trp Ala Val
            740                 745                 750

Phe Gly Tyr Glu Leu Lys Trp Tyr Trp Thr Glu Pro Glu Gln Gly Asn
        755                 760                 765

Phe Asn Tyr Arg Asp Ala Asn Glu Met Ile Glu Phe Cys Glu Arg Tyr
    770                 775                 780

Asn Ile Lys Thr Arg Gly His Cys Ile Phe Trp Glu Val Glu Ser Ala
785                 790                 795                 800

Ile Gln Pro Trp Val Gln Gln Leu Thr Gly Ser Lys Leu Glu Ala Ala
                805                 810                 815

Val Glu Asn Arg Val Thr Asp Leu Leu Thr Arg Tyr Asn Gly Lys Phe
            820                 825                 830

Arg His Tyr Asp Val Asn Asn Glu Met Leu His Gly Ser Phe Tyr Arg
        835                 840                 845

Asp Arg Leu Asp Ser Asp Ala Arg Ala Asn Met Phe Lys Thr Ala His
    850                 855                 860

Glu Leu Asp Pro Leu Ala Thr Leu Phe Leu Asn Glu Tyr His Ile Glu
865                 870                 875                 880

Asp Gly Phe Asp Ser Arg Ser Ser Pro Glu Lys Tyr Ile Lys Leu Val
                885                 890                 895

His Lys Leu Gln Lys Lys Gly Ala Pro Val Gly Gly Ile Gly Ile Gln
            900                 905                 910

Gly His Ile Thr Ser Pro Val Gly His Ile Val Arg Ser Ala Leu Asp
        915                 920                 925

Lys Leu Ser Thr Leu Gly Leu Pro Ile Trp Phe Thr Glu Leu Asp Val
    930                 935                 940

Ser Ser Thr Asn Glu His Ile Arg Gly Asp Asp Leu Glu Val Met Leu
945                 950                 955                 960

Trp Glu Ala Phe Ala His Pro Ala Val Glu Gly Val Met Leu Trp Gly
                965                 970                 975

Phe Trp Glu Leu Phe Met Ser Arg Glu His Ser His Leu Val Asn Ala
            980                 985                 990

Asp Gly Glu Val Asn Glu Ala Gly Lys Arg Phe Leu Glu Ile Lys Arg
        995                 1000                1005

Glu Trp Leu Ser Phe Val Asp Gly Glu Ile Glu Asp Gly Gly Gly Leu
    1010                1015                1020

Glu Phe Arg Gly Tyr His Gly Ser Tyr Thr Val Glu Val Val Thr Ser
1025                1030                1035                1040

Glu Ser Lys Tyr Val Thr Asn Phe Val Val Asp Lys Gly Asn Ser Pro
                1045                1050                1055

-continued

```
Val Asp Val Ile Ile Asp Leu
        1060

<210> SEQ ID NO 30
<211> LENGTH: 513
<212> TYPE: PRT
<213> ORGANISM: Arabidopsis thaliana

<400> SEQUENCE: 30

Met Lys Pro Pro Arg Ser Ser Glu Thr Lys Gly Leu Leu Gln Phe Ser
1               5                   10                  15

Arg Ser Leu Glu Asp Asp Ser Asp Glu Glu Trp Lys Ile Asp Gly Asn
            20                  25                  30

Gly Phe Ile Arg Glu Met Ala Gln Arg Ile Gln Leu His Gln Gly Asn
        35                  40                  45

Ile Tyr Ser Phe Ser Ala Trp Val Lys Leu Arg Glu Gly Asn Asp Lys
    50                  55                  60

Lys Val Gly Val Val Phe Arg Thr Glu Asn Gly Arg Leu Val His Gly
65                  70                  75                  80

Gly Glu Val Arg Ala Asn Gln Glu Cys Trp Thr Leu Leu Lys Gly Gly
                85                  90                  95

Ile Val Pro Asp Phe Ser Gly Pro Val Asp Ile Phe Phe Glu Ile His
            100                 105                 110

Thr Tyr Ile Leu Cys Val Asn Val Val Leu Met Arg Lys Gln Ser Glu
        115                 120                 125

Asn Arg Gly Ala Lys Ile Ser Ala His Asn Val Leu Leu Lys Gln Phe
    130                 135                 140

Ser Lys Glu Glu Trp Lys Leu Lys Gln Asp Gln Leu Ile Glu Lys Ile
145                 150                 155                 160

Arg Lys Ser Lys Val Arg Phe Glu Val Thr Tyr Glu Asn Lys Thr Ala
                165                 170                 175

Val Lys Gly Val Val Ile Ser Leu Lys Gln Thr Lys Ser Ser Phe Leu
            180                 185                 190

Leu Gly Cys Gly Met Asn Phe Arg Ile Leu Gln Ser Gln Gly Tyr Arg
        195                 200                 205

Lys Trp Phe Ala Ser Arg Phe Lys Ile Thr Ser Phe Thr Asn Glu Met
    210                 215                 220

Lys Trp Tyr Ala Thr Glu Lys Ala Arg Gly Gln Glu Asn Tyr Thr Val
225                 230                 235                 240

Ala Asp Ser Met Leu Lys Phe Ala Glu Asp Asn Gly Ile Leu Val Arg
                245                 250                 255

Gly His Thr Val Leu Trp Asp Asn Pro Lys Met Gln Pro Ser Trp Val
            260                 265                 270

Lys Asn Ile Lys Asp Pro Asn Asp Val Met Asn Val Thr Leu Asn Arg
        275                 280                 285

Ile Asn Ser Val Met Lys Arg Tyr Lys Gly Lys Leu Thr Gly Trp Asp
    290                 295                 300

Val Val Asn Glu Asn Leu His Trp Asp Tyr Phe Glu Lys Met Leu Gly
305                 310                 315                 320

Ala Asn Ala Ser Thr Ser Phe Tyr Asn Leu Ala Phe Lys Ile Asp Pro
                325                 330                 335

Asp Val Arg Leu Phe Val Asn Glu Tyr Asn Thr Ile Glu Asn Thr Lys
            340                 345                 350

Glu Phe Thr Ala Thr Pro Ile Lys Val Lys Lys Met Met Glu Glu Ile
        355                 360                 365
```

-continued

```
Leu Ala Tyr Pro Gly Asn Lys Asn Met Lys Gly Ala Ile Gly Ala Gln
    370                 375                 380

Gly His Phe Gly Pro Thr Gln Pro Asn Leu Ala Tyr Ile Arg Ser Ala
385                 390                 395                 400

Leu Asp Thr Leu Gly Ser Leu Gly Leu Pro Ile Trp Leu Thr Glu Val
                405                 410                 415

Asp Met Pro Lys Cys Pro Asn Gln Ala Gln Tyr Val Glu Asp Ile Leu
            420                 425                 430

Arg Glu Ala Tyr Ser His Pro Ala Val Lys Gly Ile Ile Ile Phe Gly
        435                 440                 445

Gly Pro Glu Val Ser Gly Phe Asp Lys Leu Thr Leu Ala Asp Lys Asp
450                 455                 460

Phe Asn Asn Thr Gln Thr Gly Asp Val Ile Asp Lys Leu Leu Lys Glu
465                 470                 475                 480

Trp Gln Gln Lys Ser Ser Glu Ile Gln Thr Asn Phe Thr Ala Asp Ser
                485                 490                 495

Asp Asn Glu Glu Glu Glu Val Ser Leu Leu His Gly His Tyr Asn Val
            500                 505                 510

Asn
```

<210> SEQ ID NO 31
<211> LENGTH: 536
<212> TYPE: PRT
<213> ORGANISM: Arabidopsis thaliana

<400> SEQUENCE: 31

```
Met Lys Pro Pro Arg Ser Ser Glu Thr Lys Gly Leu Leu Gln Phe Ser
1               5                   10                  15

Arg Ser Val Glu Asp Asp Ser Glu Glu Trp Lys Ile Asp Gly Ser
            20                  25                  30

Gly Ser Ile Arg Glu Met Thr Gln Arg Ile Gln Leu His Glu Gly Asn
        35                  40                  45

Ile Tyr Ser Phe Ser Ala Trp Val Lys Leu Arg Glu Gly Asn Asn Lys
    50                  55                  60

Lys Val Gly Val Val Phe Arg Thr Glu Asn Gly Arg Phe Val His Gly
65                  70                  75                  80

Gly Glu Val Arg Ala Lys Lys Arg Cys Trp Thr Leu Leu Lys Gly Gly
                85                  90                  95

Ile Val Pro Asp Val Ser Gly Ser Val Asp Ile Phe Phe Glu Val Gln
            100                 105                 110

Gln Leu Ala Ile Tyr Ser Asp Asp Lys Glu Ala Lys Ile Ser Ala Ser
        115                 120                 125

Asp Val Ser Leu Lys Gln Phe Ser Lys Gln Glu Trp Lys Leu Lys Gln
130                 135                 140

Asp Gln Leu Ile Glu Lys Ile Arg Lys Ser Lys Val Arg Phe Glu Val
145                 150                 155                 160

Thr Tyr Gln Asn Lys Thr Ala Val Lys Gly Ala Val Ile Ser Ile Glu
                165                 170                 175

Gln Thr Lys Pro Ser Phe Leu Leu Gly Cys Ala Met Asn Phe Arg Ile
            180                 185                 190

Leu Gln Ser Glu Gly Tyr Arg Asn Trp Phe Ala Ser Arg Phe Lys Ile
        195                 200                 205

Thr Ser Phe Thr Asn Glu Met Lys Trp Tyr Thr Thr Glu Lys Glu Arg
    210                 215                 220
```

```
Gly His Glu Asn Tyr Thr Ala Ala Asp Ser Met Leu Lys Phe Ala Glu
225                 230                 235                 240

Glu Asn Gly Ile Leu Val Arg Gly His Thr Val Leu Trp Asp Asp Pro
            245                 250                 255

Leu Met Gln Pro Thr Trp Val Pro Lys Ile Glu Asp Pro Asn Asp Leu
            260                 265                 270

Met Asn Val Thr Leu Asn Arg Ile Asn Ser Val Met Thr Arg Tyr Lys
            275                 280                 285

Gly Lys Leu Thr Gly Trp Asp Val Val Asn Glu Asn Val His Trp Asp
            290                 295                 300

Tyr Phe Glu Lys Met Leu Gly Ala Asn Ala Ser Ser Phe Tyr Asn
305                 310                 315                 320

Leu Ala Phe Lys Leu Asp Pro Asp Val Thr Met Phe Val Asn Glu Tyr
            325                 330                 335

Asn Thr Ile Glu Asn Arg Val Glu Val Thr Ala Thr Pro Val Lys Val
            340                 345                 350

Lys Glu Lys Met Glu Glu Ile Leu Ala Tyr Pro Gly Asn Met Asn Ile
            355                 360                 365

Lys Gly Ala Ile Gly Ala Gln Gly His Phe Arg Pro Thr Gln Pro Asn
            370                 375                 380

Leu Ala Tyr Met Arg Ser Ala Leu Asp Thr Leu Gly Ser Leu Gly Leu
385                 390                 395                 400

Pro Ile Trp Leu Thr Glu Val Asp Met Pro Lys Cys Pro Asn Gln Glu
            405                 410                 415

Val Tyr Ile Glu Glu Ile Leu Arg Glu Ala Tyr Ser His Pro Ala Val
            420                 425                 430

Lys Gly Ile Ile Ile Phe Ala Gly Pro Glu Val Ser Gly Phe Asp Lys
            435                 440                 445

Leu Thr Leu Ala Asp Lys Tyr Phe Asn Asn Thr Ala Thr Gly Asp Val
            450                 455                 460

Ile Asp Lys Leu Leu Lys Glu Trp Gln Gln Ser Ser Glu Ile Pro Lys
465                 470                 475                 480

Ile Phe Met Thr Asp Ser Glu Asn Asp Glu Glu Glu Val Ser Leu Leu
            485                 490                 495

His Gly His Tyr Asn Val Asn Val Ser His Pro Trp Met Lys Asn Met
            500                 505                 510

Ser Thr Ser Phe Ser Leu Glu Val Thr Lys Glu Met Gly Gln Arg Gln
            515                 520                 525

Val Val Arg Val Val Ile Asn Ala
530                 535

<210> SEQ ID NO 32
<211> LENGTH: 669
<212> TYPE: PRT
<213> ORGANISM: Arabidopsis thaliana

<400> SEQUENCE: 32

Met Leu Lys Glu Leu Gln Ser Ile Arg Ile Ser Gly Tyr Ile Arg Leu
1               5                   10                  15

Ala Ile Gly Leu Glu Ser His Phe Lys Thr Pro Asn Ile Pro Tyr Met
            20                  25                  30

Arg Ser Ala Leu Asp Ile Leu Ala Ala Thr Gly Leu Leu Ile Trp Leu
            35                  40                  45

Thr Glu Ile Asp Val Glu Ala Pro Pro Ser Val Gln Ala Lys Tyr Phe
```

```
         50                  55                  60
Glu Gln Val Leu Arg Asp Gly His Ala His Pro Gln Val Lys Gly Met
 65                  70                  75                  80

Val Val Trp Gly Gly Tyr Ser Pro Ser Gly Cys Tyr Arg Met Cys Leu
                 85                  90                  95

Thr Asp Gly Asn Phe Arg Asn Leu Pro Thr Gly Asp Val Trp Thr Cys
                100                 105                 110

Cys Tyr Val Asn Gly Glu Asp Phe Ala Ala Lys Gln Gln Cys Leu Glu
                115                 120                 125

Asn Pro Tyr Lys Pro Gln Tyr Asn Gly Gly Ile Ile Val Asn Pro Asp
130                 135                 140

Leu Gln Asn Gly Ser Gln Gly Trp Ser Gln Phe Gly Asn Ala Lys Val
145                 150                 155                 160

Asp Phe Arg Glu Phe Gly Gly Asn Lys Phe Val Val Ala Thr Gln Arg
                165                 170                 175

Asn Gln Ser Ser Asp Ser Ile Ser Gln Lys Val Tyr Leu Glu Lys Gly
                180                 185                 190

Ile Leu Tyr Thr Phe Ser Ala Trp Leu Gln Val Ser Ile Gly Lys Ser
                195                 200                 205

Pro Val Ser Ala Val Phe Lys Lys Asn Gly Glu Tyr Lys His Ala Gly
210                 215                 220

Ser Val Val Ala Glu Ser Lys Cys Trp Ser Met Leu Lys Gly Gly Leu
225                 230                 235                 240

Thr Val Asp Glu Ser Gly Pro Ala Glu Leu Phe Phe Glu Ser Glu Asn
                245                 250                 255

Thr Met Val Glu Ile Trp Val Asp Ser Val Ser Leu Gln Pro Phe Thr
                260                 265                 270

Gln Glu Glu Trp Asn Ser His His Glu Gln Ser Ile Gly Lys Val Arg
                275                 280                 285

Lys Gly Thr Val Arg Ile Arg Val Met Asn Asn Lys Gly Glu Thr Ile
290                 295                 300

Pro Asn Ala Thr Ile Ser Ile Glu Gln Lys Lys Leu Gly Tyr Pro Phe
305                 310                 315                 320

Gly Cys Ala Val Glu Asn Asn Ile Leu Gly Asn Gln Ala Tyr Gln Asn
                325                 330                 335

Trp Phe Thr Gln Arg Phe Thr Val Thr Thr Phe Gly Asn Glu Met Lys
                340                 345                 350

Trp Tyr Ser Thr Glu Arg Ile Arg Gly Gln Glu Asp Tyr Ser Thr Ala
                355                 360                 365

Asp Ala Met Leu Ser Phe Lys Ser His Gly Ile Ala Val Arg Gly
                370                 375                 380

His Asn Val Leu Trp Asp Asp Pro Lys Tyr Gln Pro Gly Trp Val Asn
385                 390                 395                 400

Ser Leu Ser Gly Asn Asp Leu Tyr Asn Ala Val Lys Arg Arg Val Tyr
                405                 410                 415

Ser Val Val Ser Arg Tyr Lys Gly Gln Leu Leu Gly Trp Asp Val Val
                420                 425                 430

Asn Glu Asn Leu His Phe Ser Phe Phe Glu Ser Lys Phe Gly Pro Lys
                435                 440                 445

Ala Ser Tyr Asn Thr Tyr Thr Met Ala His Ala Val Asp Pro Arg Thr
                450                 455                 460

Pro Met Phe Met Asn Glu Tyr Asn Thr Leu Glu Gln Pro Lys Asp Leu
465                 470                 475                 480
```

-continued

```
Thr Ser Ser Pro Ala Arg Tyr Leu Gly Lys Leu Arg Glu Leu Gln Ser
            485                 490                 495
Ile Arg Val Ala Gly Lys Ile Pro Leu Ala Ile Gly Leu Glu Ser His
        500                 505                 510
Phe Ser Thr Pro Asn Ile Pro Tyr Met Arg Ser Ala Leu Asp Thr Phe
        515                 520                 525
Gly Ala Thr Gly Leu Pro Ile Trp Leu Thr Glu Ile Asp Val Asp Ala
    530                 535                 540
Pro Pro Asn Val Arg Ala Asn Tyr Phe Glu Gln Val Leu Arg Glu Gly
545                 550                 555                 560
His Ala His Pro Lys Val Asn Gly Met Val Met Trp Thr Gly Tyr Ser
                565                 570                 575
Pro Ser Gly Cys Tyr Arg Met Cys Leu Thr Asp Gly Asn Phe Lys Asn
            580                 585                 590
Leu Pro Thr Gly Asp Val Val Asp Lys Leu Leu Arg Glu Trp Gly Gly
        595                 600                 605
Leu Arg Ser Gln Thr Thr Gly Val Thr Asp Ala Asn Gly Leu Phe Glu
    610                 615                 620
Ala Pro Leu Phe His Gly Asp Tyr Asp Leu Arg Ile Ser His Pro Leu
625                 630                 635                 640
Thr Asn Ser Lys Ala Ser Tyr Asn Phe Thr Leu Thr Ser Asp Asp Asp
                645                 650                 655
Ser Ser Gln Lys Gln Pro Ser Leu Tyr Val Phe Arg Val
            660                 665

<210> SEQ ID NO 33
<211> LENGTH: 329
<212> TYPE: PRT
<213> ORGANISM: Zea mays

<400> SEQUENCE: 33

Met Gly Ala Asn Asp Lys Pro Met Ala His Ala Asn Val Ser Ile Glu
1               5                   10                  15
Leu Leu Arg Leu Gly Phe Pro Phe Gly Asn Ala Val Thr Lys Glu Ile
            20                  25                  30
Leu Gly Leu Pro Ala Tyr Glu Lys Trp Phe Thr Ser Arg Phe Ser Val
        35                  40                  45
Ala Thr Phe Glu Asn Glu Met Lys Trp Tyr Ser Thr Glu Trp Thr Gln
    50                  55                  60
Asn His Glu Asp Tyr Arg Val Pro Asp Ala Met Met Ser Leu Met Arg
65                  70                  75                  80
Lys Tyr Lys Ile Lys Val Arg Gly His Asn Val Phe Trp Asp Asp Gln
                85                  90                  95
Asn Ser Gln Met Gln Trp Val Lys Pro Leu Asn Leu Ala Gln Leu Lys
            100                 105                 110
Ala Ala Met Gln Lys Arg Leu Lys Ser Val Val Ser Pro Tyr Ala Gly
        115                 120                 125
Lys Val Ile His Trp Asp Val Val Asn Glu Asn Leu His Phe Asn Phe
    130                 135                 140
Phe Glu Thr Lys Leu Gly Pro Met Ala Ser Ala Gln Ile Tyr Gln Gln
145                 150                 155                 160
Val Gly Gln Leu Asp Arg Asn Ala Ile Leu Phe Met Asn Glu Phe Asn
                165                 170                 175
Thr Leu Glu Gln Pro Gly Asp Pro Asn Pro Val Pro Ala Lys Tyr Val
```

-continued

```
              180                 185                 190
Ala Lys Met Asn Gln Ile Arg Gly Tyr Ala Gly Asn Gly Gly Leu Lys
        195                 200                 205

Leu Gly Val Gly Leu Glu Ser His Phe Ser Thr Pro Asn Ile Pro Tyr
    210                 215                 220

Met Arg Ser Ser Leu Asp Thr Leu Ala Lys Leu Lys Leu Pro Met Trp
225                 230                 235                 240

Leu Thr Glu Val Asp Val Val Lys Ser Pro Asn Gln Val Lys Tyr Leu
                245                 250                 255

Glu Gln Val Leu Arg Glu Gly Phe Ala His Pro Asn Val Asp Gly Ile
                260                 265                 270

Val Met Trp Ala Gly Trp His Ala Lys Gly Cys Tyr Val Met Cys Leu
        275                 280                 285

Thr Asn Asn Ser Phe Lys Asn Leu Pro Trp Ala Thr Ser Ser Thr Ser
    290                 295                 300

Ser Ser Pro Ser Gly Arg Arg Thr Ala Arg Pro Pro Pro Ile Thr
305                 310                 315                 320

Met Gly Arg Trp Ser Ser Thr Cys Pro
                325
```